United States Patent [19]

Baker, Jr. et al.

[11] Patent Number: 4,554,920
[45] Date of Patent: Nov. 26, 1985

[54] MICROPROCESSOR CONTROLLED CARDIAC PACEMAKER AND METHOD FOR AVOIDING PACER SUSTAINED TACHYCARDIA

[75] Inventors: Ross G. Baker, Jr.; Richard V. Calfee, both of Houston, Tex.

[73] Assignee: Intermedics, Inc., Angleton, Tex.

[21] Appl. No.: 443,830

[22] Filed: Nov. 22, 1982

[51] Int. Cl.⁴ .............................................. A61N 1/36
[52] U.S. Cl. .............................................. 128/419 PG
[58] Field of Search ................................. 128/419 PG

[56] References Cited

U.S. PATENT DOCUMENTS

| | | | |
|---|---|---|---|
| 4,284,082 | 8/1981 | Funke et al. | 128/419 PG |
| 4,304,238 | 12/1981 | Fischer | 128/419 PG |
| 4,312,356 | 1/1982 | Sowton et al. | 128/419 PG |
| 4,343,311 | 8/1982 | Markowitz | 128/419 PG |
| 4,401,119 | 8/1983 | Herpers | 128/419 PG |
| 4,421,116 | 12/1983 | Markowitz | 128/419 PG |

Primary Examiner—William E. Kamm
Attorney, Agent, or Firm—Willian Brinks Olds Hofer Gilson & Lione Ltd.

[57] ABSTRACT

A microprocessor-controlled pacemaker is programmed to extend an atrial refractory interval in response to the detection of events which could initiate a pacer sustained tachycardia. The extended atrial refractory interval ensures that a spurious atrial event resulting from retrograde conduction of a ventricle event will not cause a pace of the ventricle.

28 Claims, 19 Drawing Figures

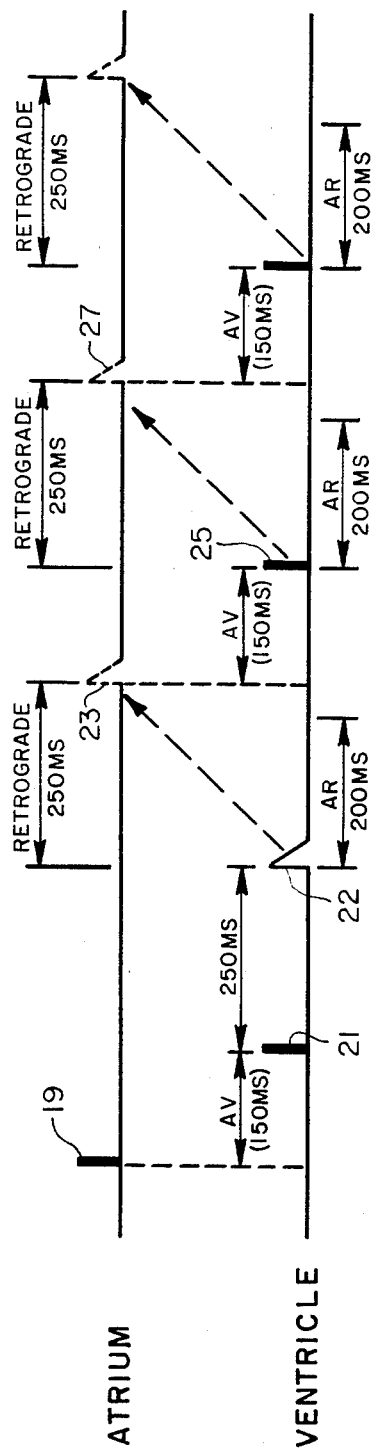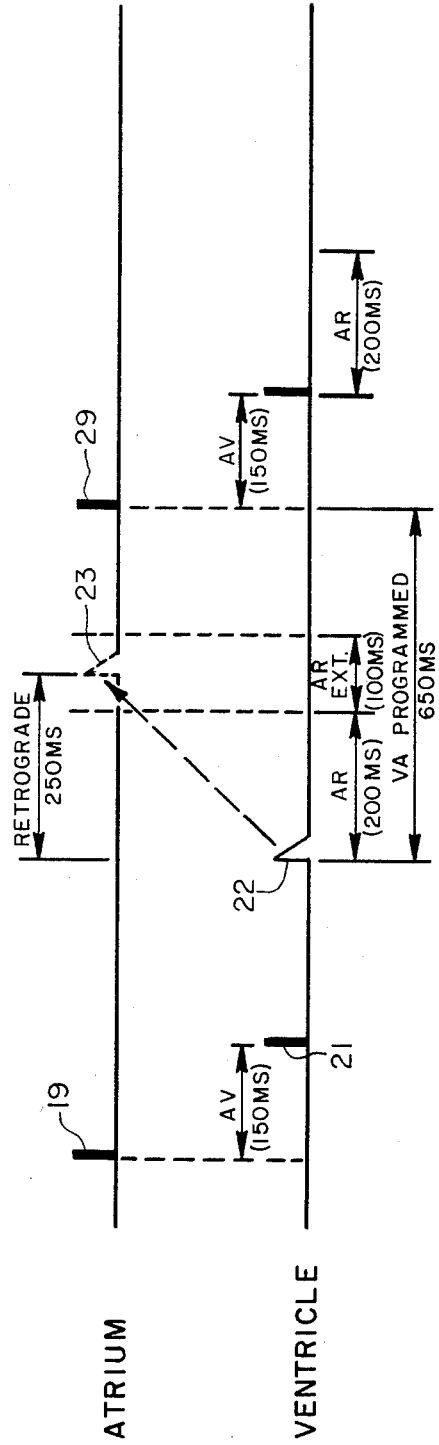

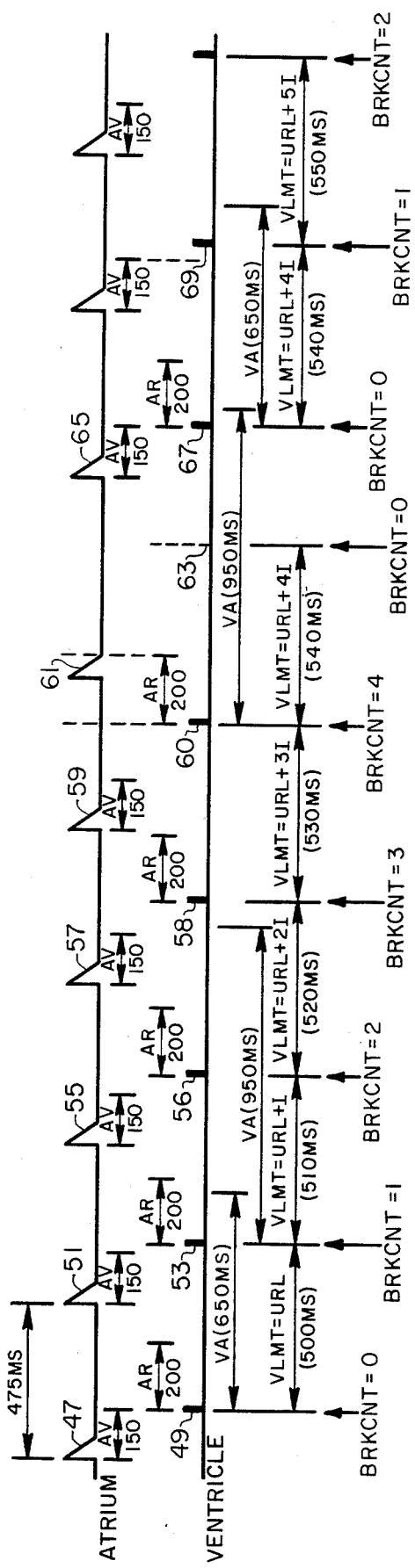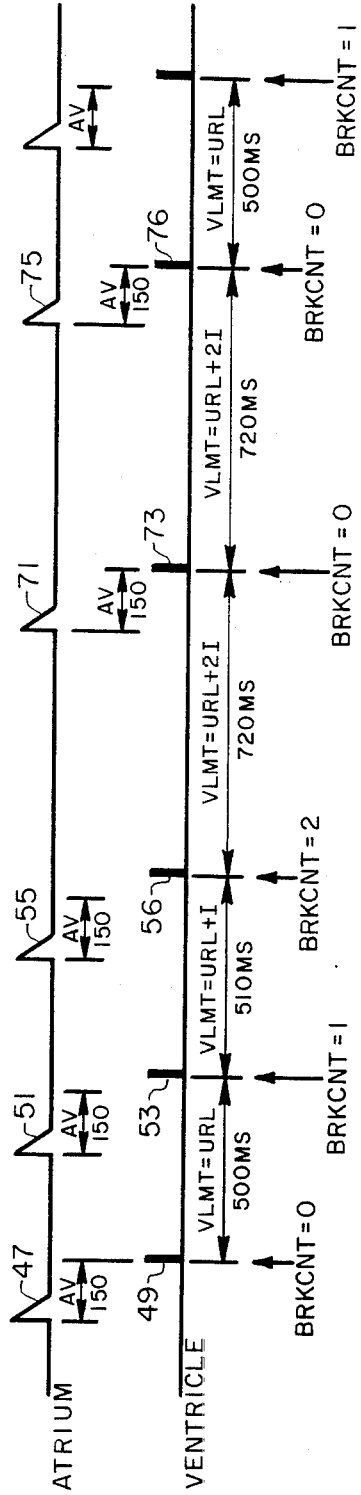
FIG. 7
FIG. 8

MICROPROCESSOR CONTROLLED CARDIAC PACEMAKER AND METHOD FOR AVOIDING PACER SUSTAINED TACHYCARDIA

TECHNICAL FIELD

The invention relates to pacemakers which are implanted in the body and are employed to monitor the operation of the heart and to stimulate heart tissue as required to maintain the proper operation of the heart. More particularly, the invention relates to a microprocessor-controlled pacemaker which operates to avoid pacer-sustained tachycardia and which further acts automatically to control the rate of ventricle stimulation in response to a sustained high intrinsic atrial rate.

BACKGROUND OF THE INVENTION

It has long been known that the heart muscle provides its pumping function in response to electrical events which occur in the atrium and ventricle of the heart. The heart is structured such that conductive tissue connects the atrium and the ventricle and provides a path for the conduction of electrical signals between the two areas. In the operation of a normal heart, a natural atrial event spontaneously occurs in the atrium and a corresponding ventricular event occurs later in the ventricle after a time interval that is typically denoted the AV interval. After the natural occurrence of the ventricular event a new atrial event naturally occurs in the atrium to trigger a succeeding ventricular event. The synchronized electrical events occurring in the atrium and ventricle cause the heart muscle to rhythmically expand and contract and thereby pump blood throughout the body.

In a diseased heart atrial and ventricular events do no naturally occur in the required synchronized manner and the pumping action of the heart is therefore irregular and ineffective to provide the required circulation of blood within the body. The required synchronized activity of such diseased hearts can be maintained by implanting a pacemaker device which applies synchronized stimulating voltage signals to either or both of the atrium and ventricle to pace the heart.

In the early stages of pacemaker development pacemakers were employed to asynchronously stimulate the ventricle of the heart without regard to natural electrical activity occurring in either the atrium or the ventricle. Although this approach had the advantage of simplicity, there was considerable risk due to the fact that paced ventricular events could interact with natural ventricular events to cause the heart to go into a dangerous fibrillation.

As the art of pacing advanced, pacemakers were provided with circuitry which sensed the occurrence of natural ventricular and atrial activity and paced the heart in either the atrium or ventricle only when required to maintain proper operation of the heart.

At the present time it is deemed desirable in some cases to operate a dual chamber pacer in what is known as the DDD mode, wherein electrical events are sensed in the atrium and ventricle and the atrium and ventricle are paced accordingly. Pacers may also be operated in the VDD mode to sense electrical events in the atrium and ventricle and to pace the ventricle. Other pacer modes of operation are employed to sense or pace in either the atrium or ventricle, as required for the particular needs of a heart.

It has been found that pacemakers which operate in the DDD or VDD modes can, under certain circumstances, sustain a dangerous tachycardia condition. A pacer sustained tachycardia condition is defined as an operational pacing state wherein the pacer erroneously stimulates the ventricle of a heart at a dangerously high rate for sustained periods of time.

Pacer sustained tachycardia is initiated when a ventricular event occurs at a time during which the connective tissue between the atrium and ventricle can transmit retrograde electrical signals from the ventricle to the atrium. The conduction of the ventricular signal to the atrium provides a spurious electrical signal in the atrium which appears to the pacer to be a natural atrial event. The pacer senses this spurious retrograde atrial signal and then paces the ventricle at a programmed AV time period following the signal. The paced ventricular signal is conducted to the atrium where it is again erroneously detected by the pacer as a natural atrial event. The pacer therefore continues to pace the ventricle at a relatively high rate defined by the sum of the programmed AV interval and the retrograde conduction time between the ventricle and atrium. This high rate is sustained indefinitely by the pacer, because retrograde conduction ensures that the pacer detects what appear to be high rate atrial events and tracks these spurious atrial events by generating corresponding high rate ventricular paces. This pacer sustained tachycardia condition overstimulates the heart, at considerable danger to the patient.

It is therefore an object of the invention to provide a pacemaker which will operate in a manner that avoids pacer sustained tachycardia.

It is a further object of the invention to provide such a pacemaker that will have a means for breaking out of any pacer sustained tachycardia that occurs.

SUMMARY OF THE INVENTION

In order to achieve the objects of the invention and to overcome the problems of the prior art, the pacemaker of the invention includes a microprocessor which is programmed to control the timing of the pacing of the ventricle and atrium. The microprocessor operates to extend the atrial refractory interval for one pacer operating cycle when a tachycardia-inducing condition is detected.

For example, if a premature ventricular contraction (PVC) is detected following a paced or sensed ventricular event, the atrial refractory period is extended so that a retrograde atrial signal generated by the PVC will fall within the refractory interval and will therefore not initiate pacing in the ventricle. The atrial refractory interval is also extended after a noise reversion, a programmed mode change, after fixed rate pacing during telemetry transmission or after leaving any pacer operational mode wherein either or both chambers are paced at a fixed rate. The atrial refractory interval is also extended in the VDD mode when the ventricle is paced in the absence of a preceding sensed atrial event.

BRIEF DESCRIPTION OF THE DRAWINGS

FIG. 2 illustrates a timing diagram of atrial and ventricular events that occur in relation to a PVC to cause pacer sustained tachycardia.

FIG. 3 illustrates a timing diagram of atrial and ventricular events and associated pacer intervals which are provided to prevent the pacer sustained tachycardia of FIG. 1.

FIG. 7 illustrates atrial and ventricular events and associated pacer intervals which are provided to reduce the ventricular pacing rate limit in response to a high atrial rate.

FIG. 8 illustrates the atrial and ventricular events and associated pacer intervals which occur to return the ventricular rate limit from a fall-back rate limit value to an upper rate limit value.

DETAILED DESCRIPTION OF PREFERRED EMBODIMENTS

Figure 1:
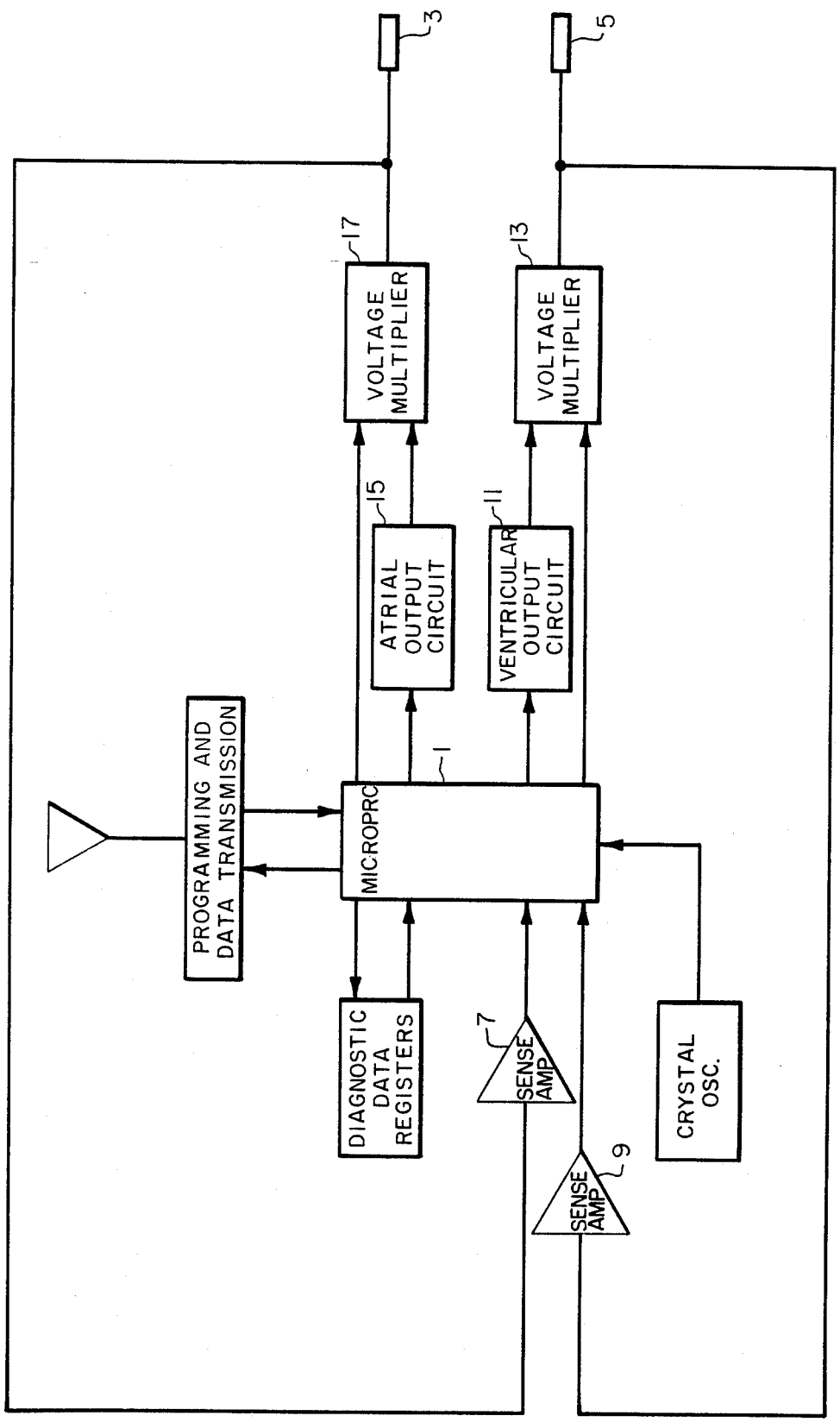
FIG. 1 illustrates a block diagram of the primary components of the cardiac pacer of the invention.

The remaining portion of the specification will describe preferred embodiments of the invention when read in conjunction with the attached drawings, in which like reference characters identify identical apparatus.

FIG. 1 illustrates a block diagram of the major components of a preferred embodiment of the pacemaker of the invention. As shown in FIG. 1, the pacemaker includes a microprocessor 1 which is programmed to apply atrial and ventricular pacing pulses to the heart in accordance with sensed atrial and ventricular conditions. In operation, an atrial electrode 3, for example of the unipolar or bipolar type, and a ventricular electrode 5 of the unipolar or bipolar type are respectively connected to the atrium and ventricle of the heart in a manner known to the art. Signals are sensed by the electrodes 3 and 5 and are applied to respective sense amplifiers 7 and 9 which then transmit amplified signals to the microprocessor 1.

In particular modes of operation, for example, the VDD mode and DDD mode, the microprocessor 1 is operated to monitor electrical signals of the atrium and ventricle. In operation, the pacer defines a VA interval which extends for a predefined time following a sensed or paced ventricular event. The pacer further defines an AV interval which extends for a predefined time following a senses or paced atrial event or from the end of the VA interval, if the pacer is operating in the VDD mode. In the VDD and DDD modes, the microprocessor 1 operates a ventricular output circuit 11 and a corresponding voltage multiplier 13 to pace the ventricle over the electrode 5. The ventricle is paced at the end of the AV interval if a ventricular event is not sensed within the interval. If a ventricular event is sensed within the interval, the ventricle is not paced at the end of the AV interval.

In the DDD mode, an atrial output circuit 15 is operated in conjunction with an associated voltage multiplier 17 to pace the atrium over the atrial electrode 3. In operation, the atrium is paced if a natural ventricle or atrial event is not sensed within the VA interval following the pacing or the sensing of a ventricular event. If an atrial event is sensed within the interval, the atrium is not paced.

In both the DDD and VDD modes, atrial refractory intervals are provided for a time following a sensed atrial event or timeout of the VA interval to a predefined time following a sensed or paced ventricular event. Any atrial events that occur within these atrial refractory intervals will be ignored by the pacer. Likewise, a ventricular refractory period is defined following a sensed or paced ventricular event. The pacer will ignore any signals detected within this ventricular refractory period.

The pacer system of FIG. 1 is capable of operating in modes other than the VDD or DDD modes. However, the VDD and DDD modes of operation are of particular interest with respect to the invention and therefore the operation of the pacing system of the invention will be described hereafter only with respect to these modes.

Pacers operating in the VDD and DDD modes can sustain a dangerous tachycardia condition as a result of retrograde conduction of signals from the ventricle to the atrium. Retrograde conduction can occur when the ventricle is paced or sensed at a time when the connecting tissue between the atrium and ventricle is conductive and when the characteristic retrograde conduction time falls outside of the atrial refractory interval of the pacer. If retrograde conduction between the ventricle and atrium occurs under such circumstances, the pacer will detect a spurious retrograde atrial event and will then lock itself in a pacing mode wherein successive retrograde atrial events trigger high rate ventricular pacing. The high rate ventricular pacing resulting from the detection of retrograde atrial events is dangerous to the patient and must be avoided or discontinued once it is initiated.

FIG. 2 illustrates a timing diagram of atrial and ventricular events which can occur to initiate retrograde conduction and an associated undesirable pacer sustained tachycardia. As shown in FIG. 2, the atrium is paced at 19 and, following a programmed AV delay, the ventricle is paced at 21. It should be understood that the ventricle is paced at the end of the AV delay because a natural ventricular event was not detected between the occurrence of the atrial event at 19 and the timing out of the AV delay at 21.

The AV delay of FIG. 2 is defined as 150 milliseconds in order to facilitate an understanding of the invention. It should be understood that the 150 milliseconds is shown for illustrative purposes and is not intended to be limiting. In operation, a pacer may typically be programmed to provide an AV delay within a desired range of, for example, 50 milliseconds to 300 milliseconds. However, other values can be employed without departing from the spirit of the invention.

Hereafter, particular representative intervals for various programmed periods will be provided as examples in order to facilitate an understanding of the invention. In every case, it should be understood that the values are provided for illustrative purposes only and are not intended to limit the scope of the invention.

As shown in FIG. 2, a premature ventricular contraction 22 (PVC) occurs approximately 250 milliseconds following the pacing of the ventricle. A PVC may be defined as a ventricular event which occurs outside of the AV interval of a preceding atrial event. The indicated 250 millisecond time period of the occurrence of the PVC is provided to illustrate a possible time frame within which a PVC could be expected to occur. However, PVC's can occur at other intervals, without departing from the spirit of the invention.

At the time of the occurrence of the PVC the tissue between the atrium and ventricle is conductive and therefore, a PVC signal is conducted from the ventricle to the atrium over a retrograde time period which can be expected to be about 250 milliseconds. Therefore, at approximately 250 milliseconds after the occurrence of the PVC in the ventricle, a retrograde atrial event 23 appears in the atrium. As shown in FIG. 2, the retrograde atrial event occurs outside of a programmed atrial refractory interval that extends, for example, for 200 milliseconds after the occurrence of the PVC.

The retrograde atrial event 23 is detected by a pacemaker operating in the VDD or DDD mode, because the event occurs outside the atrial refractory period. Thereafter the pacer times out an AV interval and paces the ventricle at 25. The signal of the paced ventricular event 25 is transmitted to the atrium by retrograde conduction to produce a successive retrograde atrial event 27 which occurs outside the atrial refractory period of the paced ventricular event 25.

It should now be understood that the above-described operation will result in the pacemaker tracking spurious retrograde atrial events and therefore pacing the ventricle at 400 millisecond intervals, or 150 beats per minute. The pacemaker will sustain this tachycardia condition for as long as there is retrograde conduction. This high rate can, of course, be very dangerous to the patient.

It should be understood that the atrial refractory interval illustrated in FIG. 2 is only a portion of a total atrial refractory interval. That is, the total atrial refractory interval extends from a sensed atrial event or end of the VA interval to a programmed time after a corresponding sensed or paced ventricular event. However, in order to facilitate an understanding of the invention, only the portion of the atrial refractory interval which extends from the ventricular event is shown. The length of this portion is programmed, for example, within the range of 200 to 570 milliseconds.

The pacemaker of FIG. 1 is operated to avoid pacer sustained tachycardia in the presence of a PVC. FIG. 3 illustrates a timing diagram of atrial and ventricular events and associated pacer timing intervals which are provided to avoid the tachycardia-inducing condition of FIG. 2.

As shown in FIG. 3, the atrial pace 19 and associated ventricular pace 21 are provided in the manner described for FIG. 2. Thereafter, the PVC 22 occurs at the time shown in FIG. 2 and is conducted to provide a retrograde atrial event 23. However, the pacer of FIG. 1 is programmed to extend the atrial refractory interval when a PVC is detected. Thus, as shown in FIG. 3, an atrial extension of, for example, 100 milliseconds, provides a total atrial refractory of 300 milliseconds and therefore covers the retrograde atrial event 23. The retrograde atrial event 23 does not cause the pacer to pace the ventricle, because the microprocessor of the pacer effectively ignores atrial events which fall within the extended atrial refractory interval. In the succeeding operational cycle of the pacemaker the atrial refractory interval is returned to its nominal programmed value of 200 milliseconds and is maintained at this value until a subsequent PVC or other tachycardia-inducing condition is sensed or another nominal atrial extension value is selected.

It should be understood that the atrial extension of 100 milliseconds was provided for illustrative purposes. The invention encompasses the use of atrial extensions less than or greater than 100 milliseconds. As a general matter, the atrial extension must be selected so that the sum of the programmed atrial refractory interval and the atrial extension is greater than the expected retrograde conduction time. Thus, for the example of FIG. 3, the sum of the atrial refractory interval and atrial extension is 300 milliseconds and this amount is clearly greater than the expected 250 millisecond retrograde conduction time.

It should be noted with respect to FIG. 3 that, after the PVC is detected, a programmed VA interval, for example, 600 milliseconds, is timed out. If an atrial event is not sensed within the programmed VA interval and the pacer is operating in the DDD mode, the atrium will be paced as indicated at 29. If an atrial event is detected within the VA interval, the atrial pace is inhibited. Of course, the AV interval is started by either the atrial pace 29 or a natural atrial event occurring within the VA interval.

Figure 4:
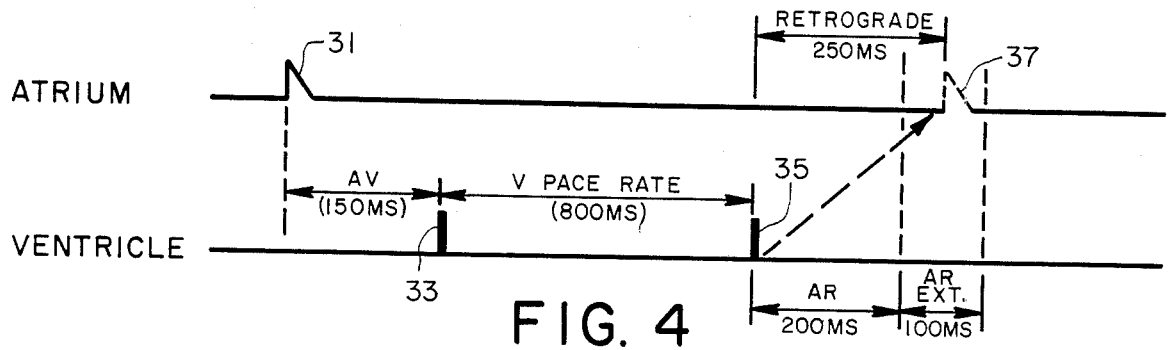
FIG. 4 illustrates a timing diagram of atrial and ventricular events and associated pacer intervals which prevent a pacer sustained tachycardia when the intrinsic atrial rate drops below a rate defined by the sum of a programmed ventricular pacing rate and a retrograde conduction time in the VDD mode of pacing.

FIG. 4 illustrates an additional tachycardia-sustaining mode. More particularly, FIG. 4 illustrates how pacer sustained tachycardia can begin under conditions of atrial Bradycardia in the VDD mode of pacing. That is, pacer sustained tachycardia can begin when the interval between successive atrial events exceeds the sum of the expected retrograde conduction time and a nominal programmed ventricular pacing rate, for example, 800 milliseconds in FIG. 4.

As shown in FIG. 4, a sensed atrial event 31 initiates a ventricular pace event 33 after an AV delay of, for example, 150 milliseconds. The atrial rate is so slow that the programmed nominal ventricular pacing interval of 800 milliseconds times out before a succeeding natural atrial event is detected. It should be appreciated in this case that the pacer is operated in the VDD mode and therefore the pacer will not pace the atrium. Accordingly, there is no sensed or paced atrial event at the end of the 800 millisecond nominal ventricular pacing interval and therefore, the ventricle is paced at 35. Retrograde conduction can occur as a result of the pace 35 because the tissue between the atrium and ventricle is conductive. Accordingly, a retrograde event 37 could appear in the atrium 250 milliseconds after the spaced ventricular event 35. Pacer sustained tachycardia can occur because the event 37 is provided outside the 200 millisecond atrial refractory interval.

As shown in FIG. 4, the pacer of the invention avoids pacer sustained tachycardia by extending the atrial refractory interval when the condition of FIG. 4 is sensed. That is, the pacer will extend the atrial refractory interval for one cycle when it is operating in the VDD mode and it paces the ventricle without having sensed a preceding triggering atrial event.

Figure 5:
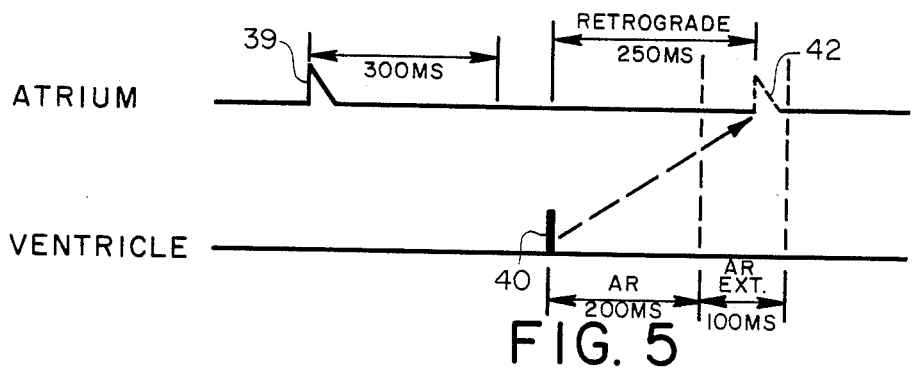
FIGS. 5, 6A and 6B illustrate timing diagrams of atrial and ventricular events and associated pacer intervals which prevent a pacer sustained tachycardia after noise reversion, when new pacing modes are programmed, and after fixed pacing during the transmission of telemetry.
Figure 6A:
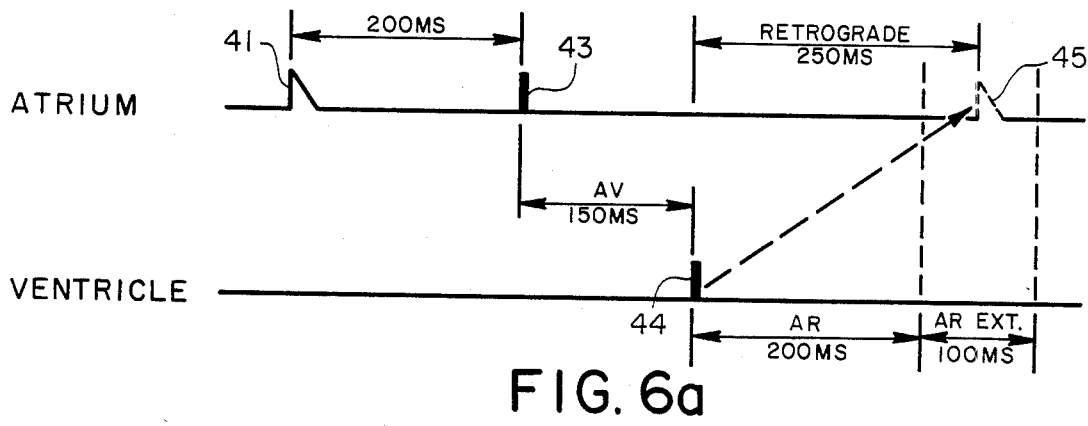
Figure 6B:
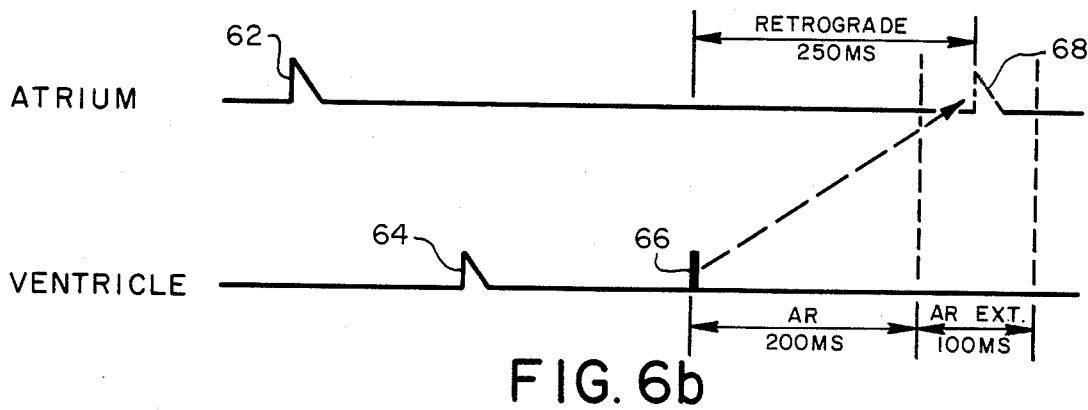

FIGS. 5, 6A and 6B illustrate the manner in which pacer sustained tachycardia can be avoided when the pacer is operating in a fixed rate mode and a new pacing mode such as the VDD or DDD mode is programmed. The illustrated conditions are also applicable for avoiding pacer sustained tachycardia after noise reversion or after fixed rate pacing during the transmission of telemetry.

As shown in FIG. 5, a natural atrial event 39 can occur while the pacer is operating in a mode where atrial events are not sensed. Thereafter the mode of the pacer is changed to VDD or DDD, where the condition of the atrium is sensed. Retrograde conduction can occur under these circumstances if the ventricle is paced or a natural ventricular event occurs at 40 after the connecting tissue of the atrium and ventricle is conductive (i.e., approximately 300 milliseconds after the last atrial event). The retrograde conduction could cause a retrograde atrial event 42 to be sensed by the pacer but the pacer will avoid a sustained tachycardia by extending its atrial refractory interval.

The pacer of the invention avoids pacer sustained tachycardia for the condition of FIG. 5 by extending the atrial refractory interval for one cycle when the pacer leaves the fixed rate pacing mode.

In FIG. 6a, a spontaneous atrial event 41 occurs and is followed by a fixed rate pace of the atrium at 43, while the atrium is still refractory. For illustrative purposes, the atrial pace 43 is shown to occur 200 milliseconds after the spontaneous atrial event 41. The ventricle is then paced after an AV delay of, for example, 150 milliseconds. The ventricular pace 44 causes a retrograde atrial event 45. As shown in FIG. 6a, the atrial refractory extension is provided when the pacer leaves the fixed rate pacing mode and therefore, pacer sustained tachycardia is avoided.

FIG. 6b shows a fixed rate pacing mode wherein a spontaneous atrial event 62 is followed by a spontaneous ventricular event 64. A fixed rate pace of the ventricle then occurs at 66 and a spurious atrial event 68 is generated as a result of retrograde conduction. Pacer sustained tachycardia is avoided by extending the atrial refractory interval when the pacer leaves the fixed rate pacing mode.

The pacer of the invention operates to pace the ventricle at a rate defined by natural atrial events, unless the rate of the atrial events exceeds a programmed ventricular rate limit. The programmed maximum ventricular rate limit corresponds to a minimum ventricular rate limit interval (VLMT). In operation, when the atrial-to-atrial signal spacing is less than the ventricular rate limit interval, the pacer will begin to pace the ventricle at the ventricular rate limit.

FIG. 7 illustrates atrial and ventricular events and associated pacer timing intervals that can occur in the presence of relatively rapid atrial events. Thus, as shown in FIG. 7, a natural atrial event 47 is detected by the pacer and, after an AV delay of, for example 150 milliseconds, the ventricle is paced at 49. Thereafter the atrial refractory interval of, for example, 200 milliseconds, times out and a succeeding atrial event 51 is detected approximately 475 milliseconds after the first atrial event 47.

It will be assumed at this point that the ventricular rate limit interval VLMT is programmed to an upper rate limit interval value (URL) of 500 milliseconds. This value is selected for illustrative purposes and is not intended to limit the scope of the invention. As an example, the upper rate limit could be set from approximately 330 milliseconds to 650 milliseconds.

After the second atrial event 51 is detected, the pacer times out the AV delay interval of 150 milliseconds and at this point the pacer might be expected to pace the ventricle. However, the ventricle is not paced at this point because the pace would fall within the defined VLMT of 500 milliseconds. Therefore, the pacer will wait to pace the ventricle at a point 53 which is 500 milliseconds (i.e., the URL interval) after the preceding ventricular pace 49.

Successive atrial events 55, 57, 59 and 61 occur at intervals of 475 milliseconds. Thus, these atrial events occur at a rate that is more rapid than the rate defined by VLMT. The pacer can be programmed to continue to pace at the URL value of VLMT in response to successive high rate atrial events. However, it has been found advantageous in some circumstances to incrementally increase the ventricular rate limit interval VLMT in the presence of a naturally high atrial rate. Accordingly, a fallback rate limit interval (FLBK) is programmed to define a low rate to which the pacer will gradually drop in the presence of high rate atrial events. For illustrative purposes the fallback rate limit interval value will hereafter be assumed to be programmed to 650 milliseconds. It should, of course, be appreciated that this value is not intended to limit the invention. For example, the pacer apparatus of the invention could be programmed to define fallback values of from 330 to 650 milliseconds, with the understanding that the fallback rate limit value should be either equal to or greater than the upper rate limit value URL.

Thus, for example, if the fallback rate value FLBK is programmed to the same value as the upper rate limit URL, the pacer will pace the ventricle at the upper rate limit for as long as high rate atrial events occur. Alternatively, if the fallback rate interval is programmed to a higher value than the upper rate limit, the ventricular rate limit interval VLMT will be incrementally increased from its initial upper rate limit value to the fallback rate limit value in the presence of high rate atrial events.

FIG. 7 illustrates atrial and ventricular timing events that can occur when the upper rate limit interval value URL is programmed at 500 milliseconds, the fallback rate limit interval FLBK is programmed at 650 milliseconds and the pacer is programmed to fall back by incrementing the ventricular rate limit interval VLMT in 10 millisecond amounts (I). The 10 millisecond increments are provided as an example to facilitate an understanding of the invention. However, it should be appreciated that other incremental amounts can be employed with departing from the invention. For example, the pacer could be programmed to define fallback increments of from 2.5 milliseconds to 100 milliseconds.

At the time that the ventricular pace 53 occurs, the ventricular rate limit interval VLMT which was previously defined as equal to URL is now incremented to URL plus I, or 510 milliseconds. Accordingly, when the atrial event 55 occurs following the atrial event 51, the ventricular rate limit interval VLMT times out to 510 milliseconds and the pacer then paces the ventricle at 56. When the ventricle is paced at 56 the ventricular rate limit interval VLMT is incremented again to 520 milliseconds and therefore, when the atrial event 57 is detected, a ventricular pace 58 is provided at an interval of 520 milliseconds.

The ventricular rate limit VLMT is increased to 530 milliseconds by the time that the ventricle is paced at 58 and thereafter the atrial event 59 results in a ventricular pace at 60 which occurs 530 milliseconds after the preceding ventricular pace at 58. When the ventricular pace 60 occurs, the ventricular rate limit VLMT is incremented to 540 milliseconds and, as for preceding ventricular pace events, the atrial refractory interval of 200 milliseconds is timed out.

The atrial event 61 occurs during the atrial refractory interval following the ventricular pace 60 and the atrial event 61 is therefore ignored by the pacer. The pacer does not pace the ventricle at the point 63 which occurs 540 milliseconds after the ventricular pace 60. This dropping of a ventricular pace is known in the art as Wenckeback behavior and is advantageous in this operation because it ensures a periodic resynchronization of the pacer at an average rate lower than the ventricular rate limit.

It should be understood that, when the ventricular pace is not delivered at 63, the pacer will be timing out a VA interval which was initiated at the previous ventricular pace 60. As explained above, if an atrial event is not detected within the VA interval, a pacer operating in the DDD mode will pace the atrium. As a practical matter, it is known that when the pacer is operating in the fallback mode, high rate atrial events are present and it therefore can be expected that an atrial event will be detected within a relatively short time after the point 63. Accordingly, it has been determined that, when operating in the fallback mode, the VA interval should be increased to allow additional time to detect an atrial event. Thus, the pacer is programmed to add an additonal delay, for example, 300 milliseconds, to the VA interval for as long as the pacer is operating at the ventricular rate limit VLMT.

Thus, with reference to FIG. 7, the VA interval immediately after the ventricular pace event 49 is defined, for example, at a nominal value of 650 milliseconds. However, by the time of the ventricular pace 53 and succeeding ventricular paces at the ventricular rate limit, the VA interval is increased to 950 milliseconds. Therefore, the VA interval extends 950 milliseconds from the ventricular pace 60, as shown in FIG. 7. The 950 millisecond VA interval is sufficient in the illustrated example to allow a succeeding natural atrial event 65 to be detected. It is therefore ensured that the pacer will track on this atrial event, provided that the atrial rate remains high.

It should be understood that the 300 millisecond increment for the VA interval is not intended to limit the scope of the invention. The 300 millisecond interval was selected as an amount that should generally provide the indicated desirable sensing of an atrial event.

The ventricle is paced at 67 after an AV delay following the sensed atrial event 65. The ventricular rate limit interval VLMT was not incremented previously, because the ventricle was not paced at the ventricular rate limit. Accordingly, the ventricular rate limit interval VLMT remains at 540 milliseconds when the ventricle is paced at 67. The ventricular rate limit VLMT is incremented to 550 milliseconds by the succeeding ventricular pace at 69.

For as long as the indicated rapid atrial events occur, the ventricular rate limit interval VLMT will continue to be incremented until it reaches the fallback rate of 650 milliseconds. At that point the ventricle will be placed at the fallback rate for as long as the rapid atrial events occur and, in addition, ventricular paces will be periodically dropped, as described above.

FIG. 8 illustrates a timing diagram of atrial and ventricular pace events which can occur to cause the pacer to leave the fallback mode described with respect to FIG. 7. Thus, as explained above, a sensed atrial event 47 initiates a ventricular pace at 49 and a successive rapid atrial event 51 results in a pace of the ventricle at a point 53 that is 500 milliseconds (i.e., the URL interval) after the pace event 49. Thereafter a ventricular pace 56 occurs in the manner described for FIG. 7.

However, if an atrial event 71 occurs at an increased interval greater than the associated ventricular rate limit interval VLMT (i.e., of 520 milliseconds in this example), the pacer will track the atrial event 71 and will pace the ventricle at 73 after the usual programmed AV delay.

The pacer is programmed to note that a ventricular sense or pace has occurred at one interval that is greater than the presently defined ventricular rate limit interval VLMT of 520 milliseconds. Moreover, at the ventricular pace 73 the ventricular rate limit interval VLMT is not increased, because the pace 73 was generated by tracking an atrial event at a rate less than the ventricular rate limit.

If a succeeding atrial event 75 is also detected at an interval greater than the defined ventricular rate limit interval VLMT of 520 milliseconds, the ventricle is paced at 76 after the AV delay. The pacer is programmed to reset the ventricular rate limit interval VLMT to the upper rate limit URL of 500 milliseconds when the second ventricular pace or sense is detected at a rate that is lower than the defined ventricular rate limit. Thus, by the time that the ventricular pace 76 is provided, the ventricular rate limit interval VLMT is again defined at the upper rate limit of 500 milliseconds. The resetting of the ventricular rate limit interval will cause the pacer to respond in the manner shown in FIG. 7, if the atrial rate subsequently increases above the rate defined by the upper rate limit interval URL.

It should be understood that the test condition of two relatively low rate ventricular paces was selected as a reasonable means for discontinuing the fallback mode when atrial events move from a rate above the defined ventricular rate limit to a rate below the ventricular rate limit. Other numbers of ventricular senses or paces at a reduced rate could be employed as a condition for resetting the ventricular rate limit, without departing from the spirit of the invention. It should now be understood that the operation described in FIG. 8 provides a means for exiting from the fallback mode when the atrial rate drops to within the tracking limits of the pacer.

Although the pacer operates to avoid pacer-induced tachycardia, it is nevertheless possible in rare instances for the pacer to maintain tachycardia as a result of retrograde conduction from the ventricle to the atrium. Accordingly, it is necessary to provide a means for breaking out of pacer induced tachycardia, if it should occur.

Figure 9:
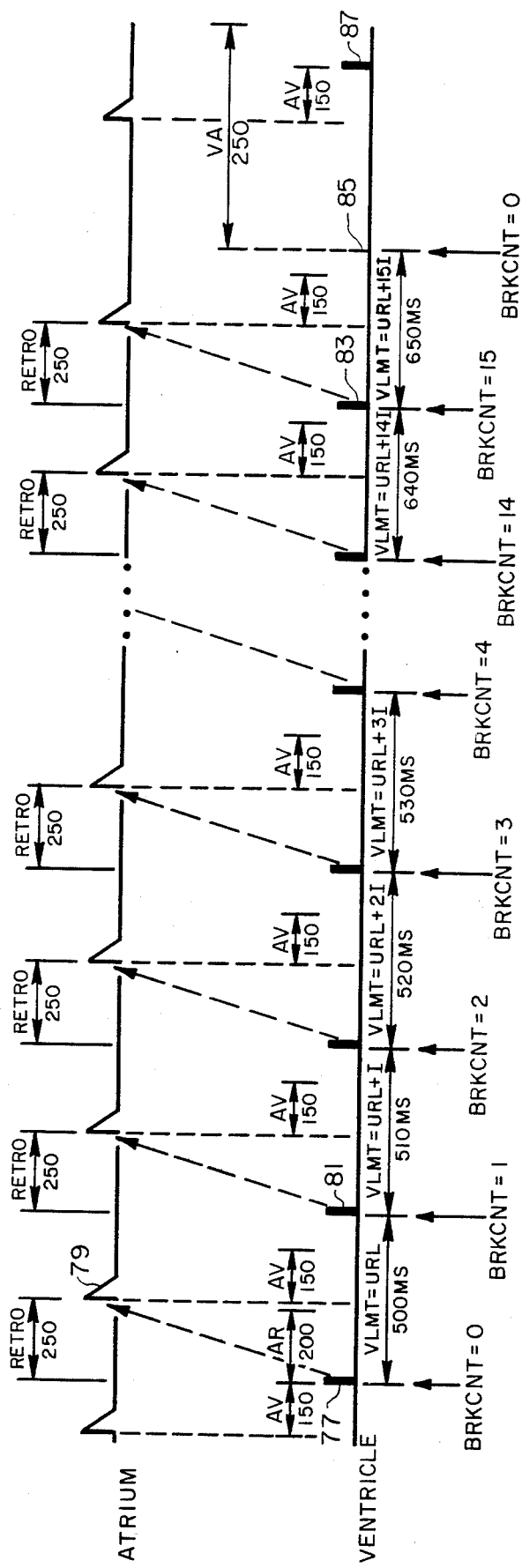
FIG. 9 illustrates atrial and ventricular events and pacer intervals which occur when the pacer operates to break out of a pacer sustained tachycardia.

FIG. 9 illustrates a timing diagram for atrial and ventricular events and associated pacer intervals which occur when the pacer breaks out of a tachycardia sustaining condition. As shown in FIG. 9, it is assumed that a tachycardia is started with a ventricular pace at 77 which provides a spurious atrial event 79 by retrograde conduction. As explained above with respect to FIG. 2, successive retrograde conduction and triggering of ventricular pacing results in an atrial-to-atrial event interval of 400 milliseconds, which is less than the defined upper rate limit interval URL for the pacer. Therefore, as explained with respect to FIG. 8, the pacer will operate in the fallback mode to incrementally increase the ventricular rate limit interval VLMT to the fallback interval FLBK.

When the pacer is operating in the fallback mode, it counts each ventricular pace that occurs at the ventricular rate limit interval VLMT. Thus, the first ventricular pace 81 at the ventricular rate limit interval VLMT causes a count variable BRKCNT to be incremented to one. Successive ventricular paces increment the count until a count of fifteen is reached as a result of the ventricular pace which occurs at 83. When the count of 15 is reached, the pacer inhibits the next succeeding ventricular pace at the point 85 and resets the count to zero at this point.

The pacer avoids retrograde conduction by dropping a single ventricular pace at 85 and can therefore track the next natural atrial event that occurs or can pace the atrium (i.e., if the pacer is operating in the DDD mode) if an atrial event is not sensed after a VA delay that is initiated at the point 85.

It should be appreciated that the mode of FIG. 9 will probably usually occur in the event of a pacer sustained tachycardia and it therefore cannot be assumed that a natural high rate atrial event will occur following the dropped ventricular pace at 85. There is therefore no reason to maintain the VA interval at its extended value of 950 milliseconds.

It should be understood that the ventricular rate limit interval VLMT will not be increased when a ventricular event is inhibited to break out of a pacer sustained tachycardia condition. In the case of the timing diagram of FIG. 9, the ventricular rate limit interval would also not be increased because the fallback rate was reached at the point 83. In addition, the pacer counts the interval between the ventricular event 83 and a ventricular event 87 following the inhibited ventricular pace 85 as an interval greater than the ventricular rate limit interval VLMT. Accordingly, if a ventricular event following the ventricular pace 87 occurs at an interval that is also greater than the ventricular rate limit interval, the ventricular rate limit interval VLMT will be reset to the upper rate limit URL of 500 milliseconds, as described with respect to FIG. 8.

It should now be understood that the pacer of the invention operates to avoid pacer sustained tachycardia and also provides a means for breaking out of pacer sustained tachycardia if it occurs. Moreover, the pacer of the invention operates to reduce the ventricular pacing rate in the presence of high rate atrial events and furthermore operates in a Wenckebach fashion to ensure resynchronization of the pacer at an average ventricular rate less than the defined ventricular rate limit.

It is within the realm of possibility that a pacer could be designed with logic circuit hardware which operates to provide the logic functions necessary to operate the pacer in the above-described advantageous pacing modes and in other modes required for a modern pacer. However, given the complexity of the logic decisions required for such an advanced pacing system, it is preferred to provide a pacer that is controlled by a relatively low power microprocessor. This preferred pacer also provides an increased flexibility of design, because pacing features of the pacer can be easily modified by modifying an operating program, rather than by having to redesign logic hardware.

Thus, as shown in FIG. 1, preferred pacing apparatus is controlled by a microprocessor 1 that is programmed to achieve the above-described functions. The programming of the processor will hereafter be described with respect to a series of flowcharts which illustrate the logical decisions that are required for a multi-mode pacer which operates to provide the features of the invention.

It should be appreciated that the flowcharts represent a preferred method by which programming of the pacer can be achieved. However, the described program is not intended to limit the scope and range of the invention.

Figure 10:
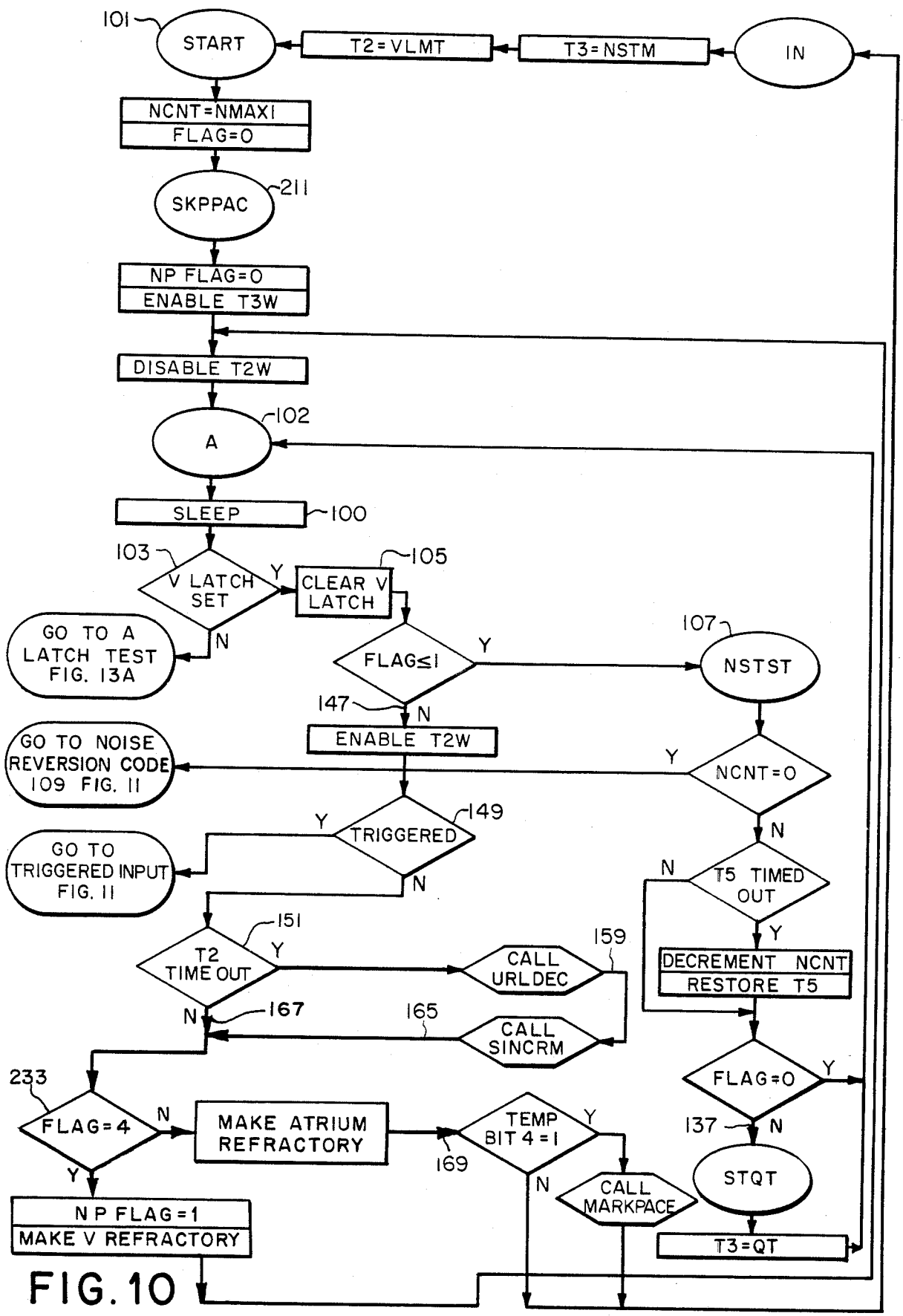
FIGS. 10–17 are flow charts of microprocessor program steps required to implement the pacing system of the pacemaker of the invention.

FIG. 10 illustrates a portion of a flowchart for a microprocessor program which operates to provide the features described above. In general, it should be understood that the microprocessor operates to minimize power consumption by periodically maintaining what will hereafter be referred to as a "sleep state." In the sleep state the microprocessor is essentially turned off and is not executing code, while various timers are operating and ventricular and atrial sensors are operating to determine "wake up" conditions at which the microprocessor is turned on to execute code and to thereby provide the logic decisions for operating the system. The program of the system is divided into operational states which designate particular operational conditions of the pacer system. The operational state of the pacer is indicated by the contents of a variable designated FLAG.

The program interrogates FLAG at various points in the program code to determine the operational state of the pacer. Several timers are interrogated to time various logic decisions within the code. Also, external conditions are indicated by latches which register the occurrence of atrial or ventricular events.

With reference to FIG. 10, pacer operation will be assumed to start with the microprocessor in its sleep state, as designated at the sleep point 100. In this state all logic operation of the microprocessor is terminated and the microprocessor is awakened only upon the occurrence of particular predefined wake up events.

For purposes of discussion at this point, it shall be assumed that the microprocessor has reached the sleep state after either pacing or sensing a ventricular event. The processor has therefore passed through the START point 101 on its way to initiate the sleep state and has further set the noise event count NCNT equal to a predetermined maximum number of noise sense events NMAXI which may be, for example, 9. FLAG has been set to zero to indicate that the pacer system is operating in state 0, which is a noise sense time. A nonphysiological flap NP FLAG has been set to zero to indicate that the program has not detected a ventricular event in the nonphysiological test interval. A wake up bit T3W is enabled so that a timer T3 will wake up the pacer when it times out a noise sense interval of, for example, 136 milliseconds. The counter T3 has been previously set as a result of the pace or sense in the ventricle and is therefore timing to its time out condition. The pacer rests in its sleep state at 100 with the above conditions having been set and also with a wake up bit T2W having been turned off, so that any time out of an associated timer T2 will not wake up the pacer.

If a ventricular event is sensed before T3 times out, pacer hardware sets a ventricular latch V LATCH and the microprocessor is awakened. The processor therefore leaves its sleep state 100 and, as shown in FIG. 10, executes a test request at 103 that interrogates the condition of V LATCH. Since V LATCH is set, the program clears the V LATCH at 105 and then determines if the microprocessor system is operating in the noise sense time (i.e., FLAG=0) or a "quiet time" state designated by FLAG=1. Since FLAG has been previously set to zero, the program will branch to the point 107 to execute noise test code, which will indicate whether the signal which was sensed in the ventricle is noise.

As shown in FIG. 10, the program initially tests the variable NCNT. If NCNT is zero, noise is detected and the program therefore branches to a point 109 of FIG. 11 to execute noise reversion code. If NCNT is nonzero, noise has not been identified and the program therefore moves to test a noise detect timer T5 to determine whether the timer has timed out. The timer T5 may be set to time out any desired noise sensing interval. For illustrative purposes, it shall be assumed that T5 is set to time out a 10 millisecond interval. In the first pass through the noise sense code, the timer T5 has timed out and therefore NCNT is decremented to 8 and T5 is reset to begin timing out a new 10 millisecond interval.

After the timer T5 is set to begin timing, the status of FLAG is checked and, since FLAG still equals zero, the processor is returned to its sleep state. If another ventricular event is detected, the hardware of the pacer again sets V LATCH and wakes up the processor. When the processor wakes up, it checks V LATCH and, upon finding that it is set, branches to clear V LATCH at 105, tests FLAG and, since FLAG is zero, branches to the noise test code at 107. As explained above, NCNT has been previously decremented to 8 and therefore, since NCNT is nonzero, T5 is checked. If T5 has timed out, NCNT is decremented again. Thereafter T5 is restored to begin timing its 10 millisecond interval and the processor is returned to its sleep state.

Figure 11:
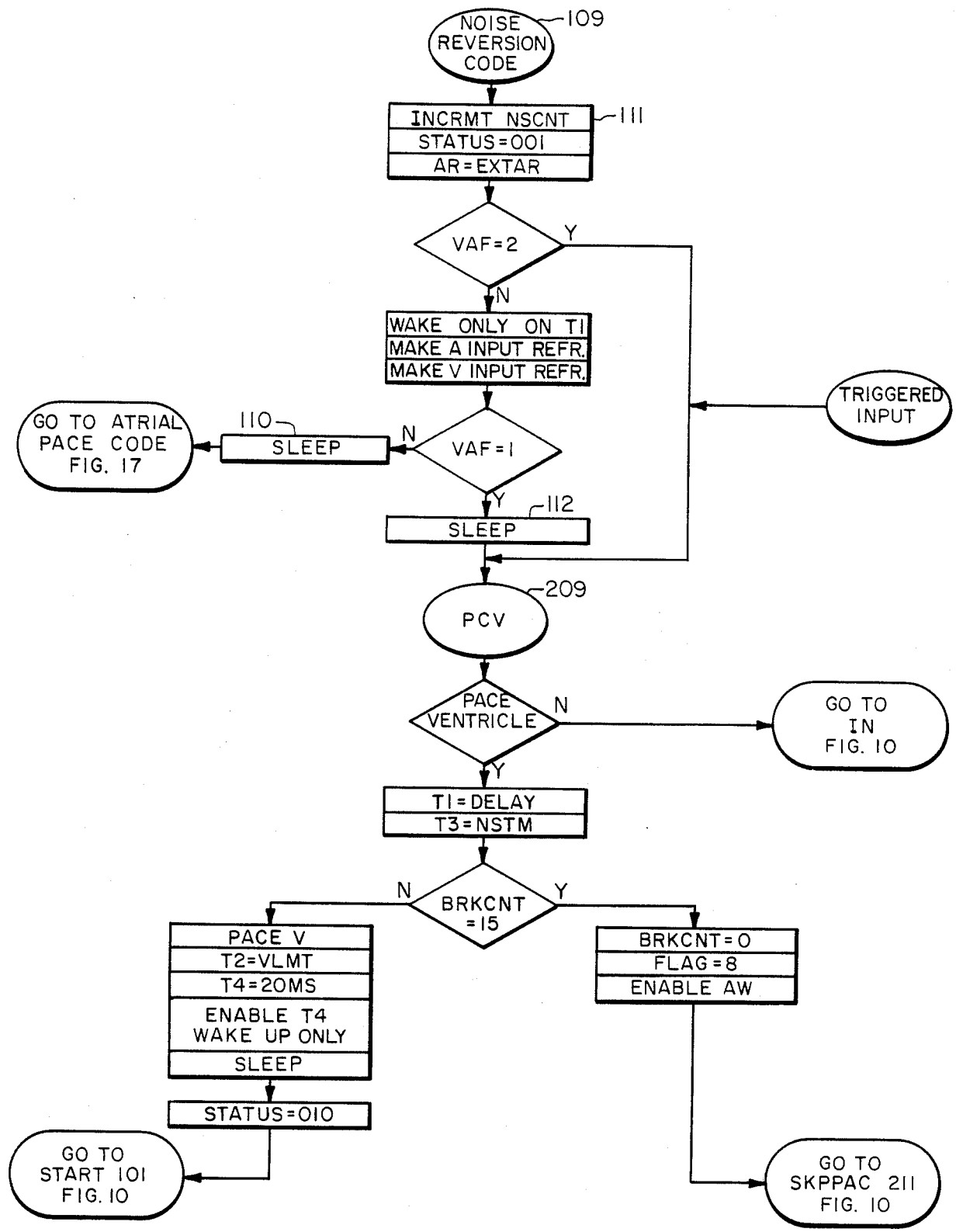

If additional noise spikes are detected in the above-described manner, NCNT will be successively decremented to zero and program control will be transferred to 109 of the noise reversion code of FIG. 11. In this event the programmed atrial refractory interval in the variable AR will be extended at 111 to a programmed extended value EXTAR. EXTAR is equal to the sum of the original programmed atrial refractory interval and a selected atrial refractory extension. As explained with respect to the timing diagrams of FIGS. 3, 5, 6A and 6B, the atrial refractory extension is made in the noise reversion mode.

Figure 17:
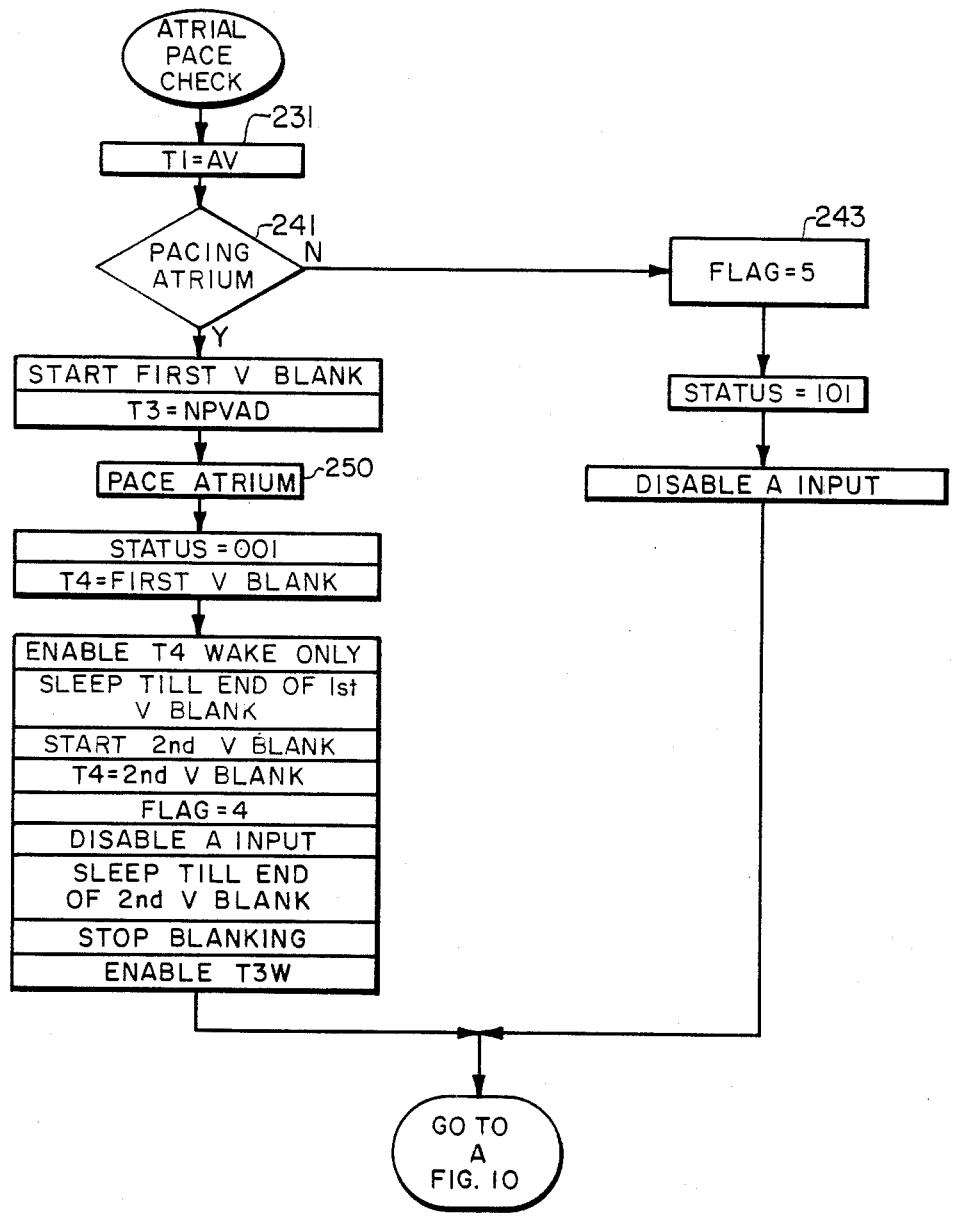

In the noise reversion mode, all time out conditions are disabled, except for a timer T1 time out, a noise counter NSCNT is incremented to indicate that a noise incident has been detected, a status indicator STATUS is set to 001, the logic circuitry for the atrial and ventricular sense amplifiers is made refractory and a check is made of a variable VAF to determine if the timer T1 is timing either the AV or VA delay. If VAF equals 2, the timer T1 has timed out the AV delay. However, if VAF equals 1, the timer T1 is currently timing the AV delay and if VAF is equal to 0, the timer T1 is timing the VA delay. In this case, it may be assumed for illustrative purposes that the noise condition was detected while T1 was timing the VA interval from the previous pacing cycle (i.e., VAF is 0). The pacer is therefore returned at 110 to the sleep state. When T1 times out the VA delay, the microprocessor wakes up and transfers to an atrial pace program segment at FIG. 17. The code of this segment is executed to begin timing the AV delay with the timer T1 and to asynchronously pace the atrium if the pacer is operating in the DDD mode. If the pacer is not operating in the DDD mode, the program will transfer to the point 243 to define a FLAG of 5, a STATUS of 101 and to disable the atrial amplifier, because the atrium will not be paced. The pacer is thereafter returned to the sleep state to await the timing out of the AV delay. It should be noted that, for as long as noise is detected, the pacer will asynchronously pace the atrium (in the DDD mode) and the ventricle.

If the noise reversion program segment of FIG. 11 is entered when the timer T1 is timing out an AV delay, VAF will be equal to one and the microprocessor will therefore be put to sleep at 112. When T1 times out the AV delay, the processor wakes up, verifies that the ventricle should be paced, sets the timer T3 to its noise sense period of, for example, 136 milliseconds, and checks a variable BRKCNT to determine if the ventricle has been paced fifteen times at the defined ventricular rate limit, as discussed with respect to the timing diagram of FIG. 9. If it is assumed at this point that BRKCNT is not equal to fifteen, then the ventricle is paced, a timer T2 is set to time the contents of VLMT, the processor apparatus is configured so as not to wake up for another sensed ventricular event and the processor is then put in a sleep state, to be awakened only by the timing out of a timer T4 which times a short capacitor discharge and blanking interval of, for example 20 milliseconds. After the interval is completed, the status register STATUS is set to 010 and program control is returned to START 101, as shown in FIG. 10. Thereafter NCNT, FLAG, and the T3W and T2W bits are set as described above and the processor is returned to its sleep state.

If the pacer is operated in the 136 millisecond noise sense time without sensing noise, it is awakened by the timing out of the T3 timer. Therefore, the processor wakes up and checks V LATCH. Assuming that no ventricular event has been detected, the processor then goes to check A LATCH. Since no atrial event can be detected, the processor next checks the status of the timer T3 at 113 of FIG. 13A to determine if the timer has timed out. Since T3 has timed out, program control is transferred to a FLAG test at 115 at which it is determined that FLAG is 0. Control is therefore transferred to the start quiet time program segment STQTM at 117 of FIG. 12. The introduction of program control to the code of FIG. 12 starts the "quiet time" state of the processor. Thus, FLAG is set to 1 to indicate that the processor is operating in its quiet time and the timer T3 is set to begin timing a quiet time interval, QT, of, for example, 64 milliseconds.

Thereafter, various tests are conducted to determine if the pacer is being operated in a mode wherein temporary parameter values are to be applied to the pacer. For example, such temporary values include a temporary atrial or ventricular pulse width or sense and amplitude word. If the pacer is not being programmed with temporary data, program control is transferred to load data which defines the parameters of the output stimulation pulses and the input sensitivity of the amplifiers of the pacer. At this point the atrial and ventricular sense amplifier circuitry is made refractory. A telemetry control bit TELEM CNT of the pacer is then tested to determine if the pacer is being operated to transmit telemetry. If TELEM is 0, telemetry is to be transmitted and the atrial refractory interval AR is therefore extended to EXTAR, as explained with respect to the timing diagrams of FIGS. 3, 5, 6A and 6B. The processor then operates to transmit telemetry and to pace the heart at a fixed rate. Program control is returned for normal operation when the telemetry mode is completed.

If the telemetry mode is not selected, a control variable TCNTL1 is tested. If TCNTL1 is not equal to zero, there has been a new mode command and therefore program control is transferred to load the new selected pacer mode TCNTL1 into a variable CNTRL1 and TCNTL1 is thereafter cleared. The atrial refractory interval AR is then extended to EXTAR, due to the programmed mode change. This extension of the atrial refractory interval is necessary in order to avoid pacer sustained tachycardia, as explained with respect to FIGS. 3, 5, 6A and 6B.

If there has not been a mode change, TCNTL1 is equal to zero and therefore control is passed to code which checks the contents of the status register STATUS. If STATUS is equal to 011, it is known that during the previous timing cycle the pacer did not sense in the atrium and paced in the ventricle. If this is the case, the timer T1 is set to begin timing the VA delay which is defined after a ventricular pace. Thereafter, an X register is set equal to the address of a three byte diagnostic counter which is employed to count the occurrence of the event indicated by a STATUS value of 011. Thereafter, program control is transferred to a test at 121 which determines if the VDD mode has been selected. If the VDD mode has been selected, the atrial refractory interval is extended at 123 to avoid pacer sustained tachycardia under the condition defined with respect to FIG. 4. That is, the atrial refractory interval is extended when the pacer is operating in the VDD mode and it has been determined (by testing the status register) that the ventricle has been paced without having been triggered by a previous atrial event.

A subroutine INCR is then called to increment the diagnostic register which is addressed by X. The register is not incremented if it would overflow as a result of the increment or if another diagnostic register which may be incremented by the subroutine has previously reached its overflow point. The STATUS register is thereafter set to 000, the VAF bit is set to zero and the NCNT variable is set to a value of NMAX2, which defines a minimum number of sense events during the quiet time which will be recognized as noise. It should be understood that VAF is set equal to zero to indicate that T1 is timing a VA delay. Thereafter the logic circuitry for the atrial and ventricular input amplifiers are enabled by code generally designated ENBLA and ENBLV. Control is then returned to a control point 102 of FIG. 10 and the processor is therefore put to sleep.

Figure 12:
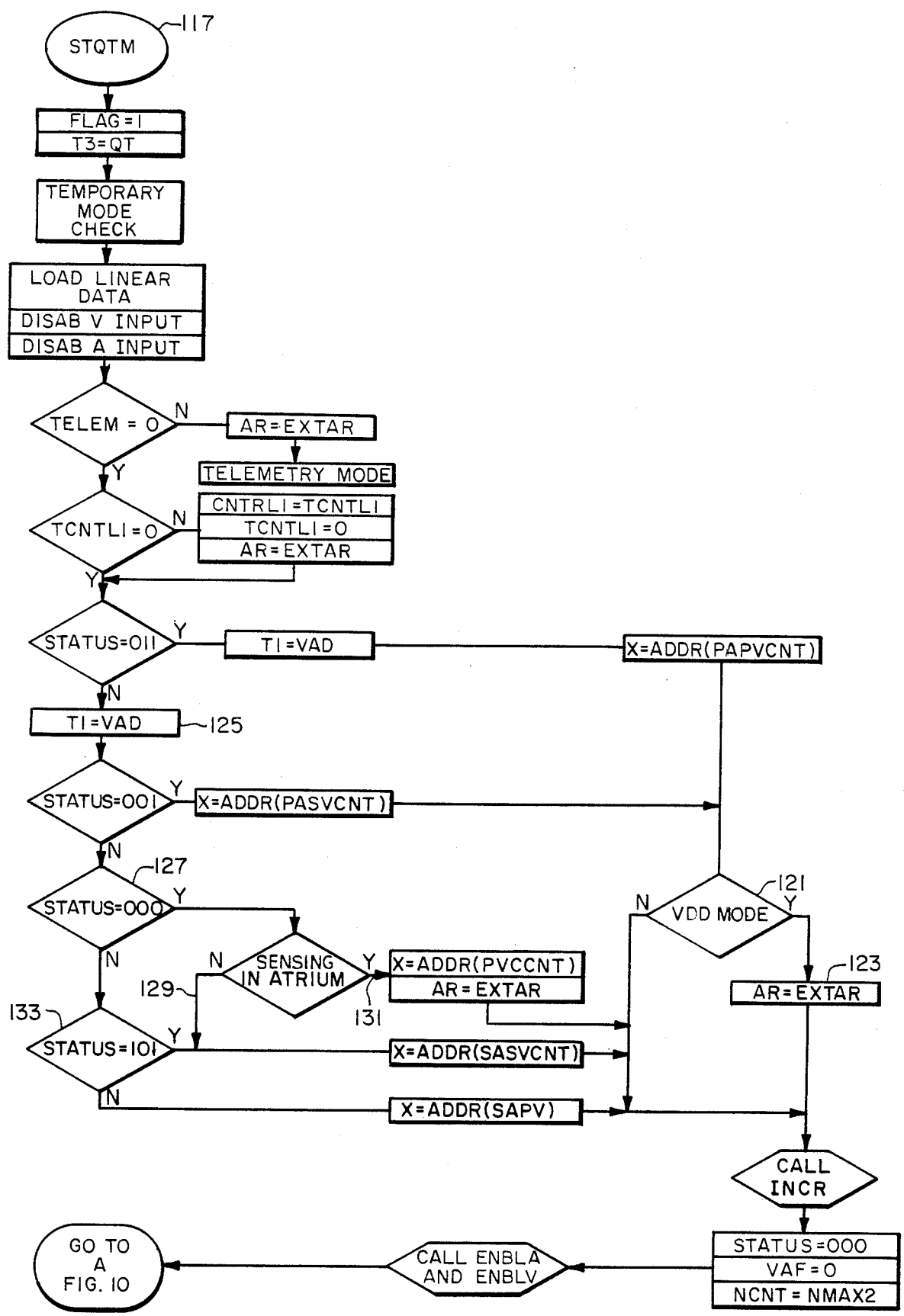

With reference to FIG. 12, if the status register is not equal to 011, program control is transferred to a point 125 at which the timer T1 is loaded with a VA interval that is longer than the above-described VA interval after a pace. The longer interval after a sense event is provided in the VVI and AAI operational modes of the pacer only if rate hysteresis is desired.

After the T1 timer is loaded, the STATUS register is checked again. If status is equal to 001, it is known that the pacer has paced in the atrium and has thereafter sensed in the ventricle. In this case the X register is loaded with an address of a three byte diagnostic counter which indicates for the DDD mode that the atrium has been paced and the ventricle has been sensed. For the VDD mode the diagnostic counter indicates that there has been no sense in the atrium and there has been a sense in the ventricle. Thereafter, at the point 121 the operational mode of the pacer is again tested. If the pacer is operating in the VDD mode, the atrial refractory interval AR is extended at 123 to avoid a pacer sustained tachycardia condition, under the condition that there has been no atrial event which preceeds a sensed ventricular event. Program operation is thereafter continued in the above-described manner.

If, with respect to FIG. 12, STATUS is not equal to 001, it is tested at 127 and, if it is equal to 000, it is known that a ventricular event has been sensed outside a programmed AV interval. Thus, it is known that a PVC has been detected. If the pacer mode is such that there is no sensing in the atrium, program control is transferred to the point 129, because the program cannot tell if the sensed ventricular event is a premature ventricular contraction. However, if the pacer is sensing in the atrium, program control is transferred to the point 131 to indicate that a ventricular event has been detected when there is no corresponding sensed atrial event and, therefore, the ventricular event is a PVC. Thus, the atrial refractory interval AR is extended to EXTAR to avoid pacer sustained tachycardia, as discussed with respect to FIGS. 2 and 3. The X pointer is loaded with the address of a diagnostic counter which counts the PVC event. Program control is then transferred to increment the diagnostic counter, to clear STATUS and the VAF bit, to set NCNT to NMAX2 and to enable the atrial and ventricular input amplifiers as discussed above.

If STATUS is not equal to 000, control is passed to 133 to determine if it is equal to 101. If it is equal to 101, there has been a sensed atrial event and a corresponding sensed ventricular event and there is therefore no need to pace either the atrium or the ventricle. X is loaded with the address of a diagnostic counter which counts this event. Program control is then transferred, as described above. If status is not equal to 101, an atrial event has been sensed and the ventricle has been paced. X is therefore loaded with the address of a diagnostic register which counts this event and program control is then transferred as indicated above.

It should now be understood that the abovedescribed STATUS check program segment is provided to set diagnostic counters which indicate the status of pacer operation. This is done so that the history of pacer operation can be determined, for example by a physician.

It should be understood that the noise sense interval (i.e., state zero), the quiet time interval (i.e., state 1) and the atrial refractory interval AR are successive portions of an atrial refractory interval which extends from a paced or sensed ventricular event.

For as long as the pacer is operating in the quiet time, FLAG is set equal to 1. Therefore, when the pacer returns to the sleep state after having passed through the program steps of FIG. 12, it may be awakened by sensed atrial or ventricular events which occur in the quiet time. If a ventricular event occurs in the quiet time, the microprocessor wakes up and detects the setting of the V LATCH. The processor therefore clears the latch as shown in FIG. 10 and moves to the noise sense code at 107 to check the timer T5 and decrement the variable NCNT in the manner described above. However, after the timer T5 is restored to start timing the 10 millisecond noise recognition interval, FLAG is tested and program control is then transferred to set T3 to begin timing an additional 64 millisecond quiet timer QT. The pacer is then put in the sleep state, where it can be awakened by sensed signals. If nine of such signals are detected, the variable NCNT is decremented to zero and program control is transferred to the noise reversion code of FIG. 11. Detection of atrial events can cause the same noise detection operation. As explained above, the atrium in the DDD mode and the ventricle are thereafter paced at a fixed rate for as long as noise is detected.

Figure 13A:
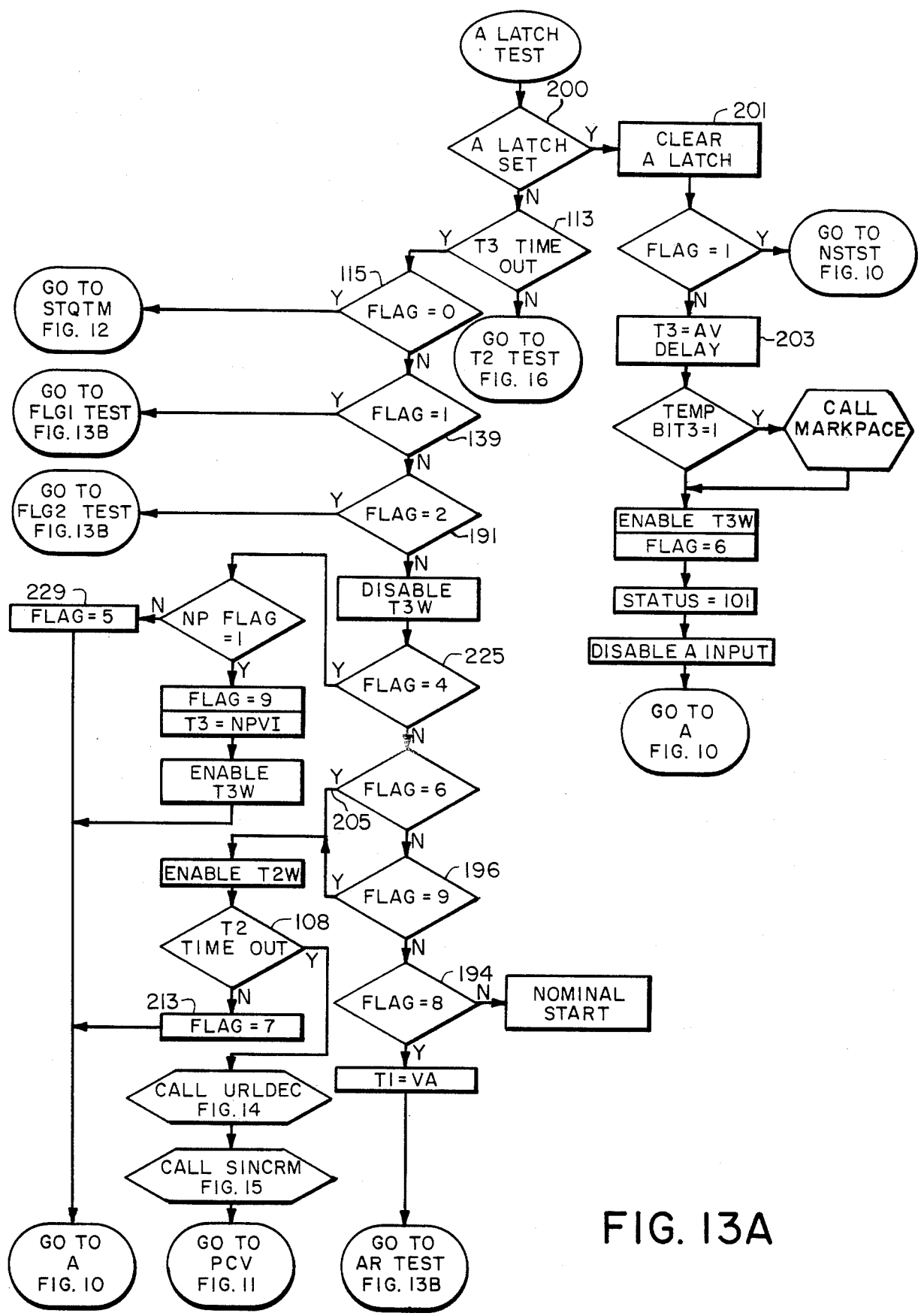

If no signal is sensed during the quiet time, the timer T3 will time out its 64 millisecond interval and the microprocessor will then wake up and move to the T3 test 113 of FIG. 13A. If T3 has timed out, program control is transferred to the FLAG test at 115. Since FLAG is now equal to 1, program control is next transferred to the FLAG test at 139. Program control is thereafter transferred to a test at 141 of FIG. 13B, wherein it is determined whether or not the pacer is sensing in the ventricle. If T3 has timed out and the pacer is sensing in the ventricle, the voltage input on the ventricular sensing lead is checked at 143 and, if the voltage is high, the quiet time is continued (by transferring to the point 107 of FIG. 10) until the voltage drops. The sensed high voltage could indicate that the pacer is in the middle of a sensed ventricular event and it is therefore necessary to allow additional quiet time to wait for the completion of the ventricular event. If the voltage on the ventricular sensing lead is not high, the program next determines at 145 whether or not the pacer is sensing in the atrium. If the pacer is sensing in the atrium, the voltage on the atrial lead is checked and, if it is high, the quiet time is continued to allow sufficient time for the sensing of the atrial event to be completed. If the voltage on the atrial input lead is not high, the atrial refractory interval AR is checked to determine if the atrial channel should remain refractory after ventricular sensing begins. If AR is not equal to zero the program will begin an atrial refractory period that extends beyond the end of the ventricular refractory period.

If the atrial refractory interval is zero, it is set to its nominal programmed value PROGAR for the next cycle, FLAG is set to 3 to indicate a program sense period following the AR interval. The wake up bit T3W of the counter T3 is then disabled because T3 at this point is not timing a relevant interval. Thereafter the microprocessor is returned to its sleep state.

If the microprocessor is sleeping when FLAG is equal to 3, it is awakened by the timer T1 timing out the VA interval or by a sensed ventricular or atrial event. If a ventricular event occurs, the microprocessor will wake up and the V LATCH test at 103 of FIG. 10 will indicate that a ventricular event has been sensed. The V LATCH will thereafter be cleared and, since FLAG is 3, the bit T2W will be enabled at 147 so that the timing out of the timer T2 can be tested. At 149 the pacer thereafter checks to see if it is operating in the AAT or VVT mode. If the pacer is operating in either of these modes, program control is transferred to the code of FIG. 11 to pace the appropriate chamber of the heart. However, if the pacer is operating in the VDD or DDD modes, program control is passed to a T2 timer test at 151. It should be understood at this point that the timer T2 is employed to time the ventricular rate limit (VLMT) for the pacer. If T2 has timed out, it is known that the pacer is in an interval which extends beyond the presently defined ventricular rate limit interval.

Figure 14:
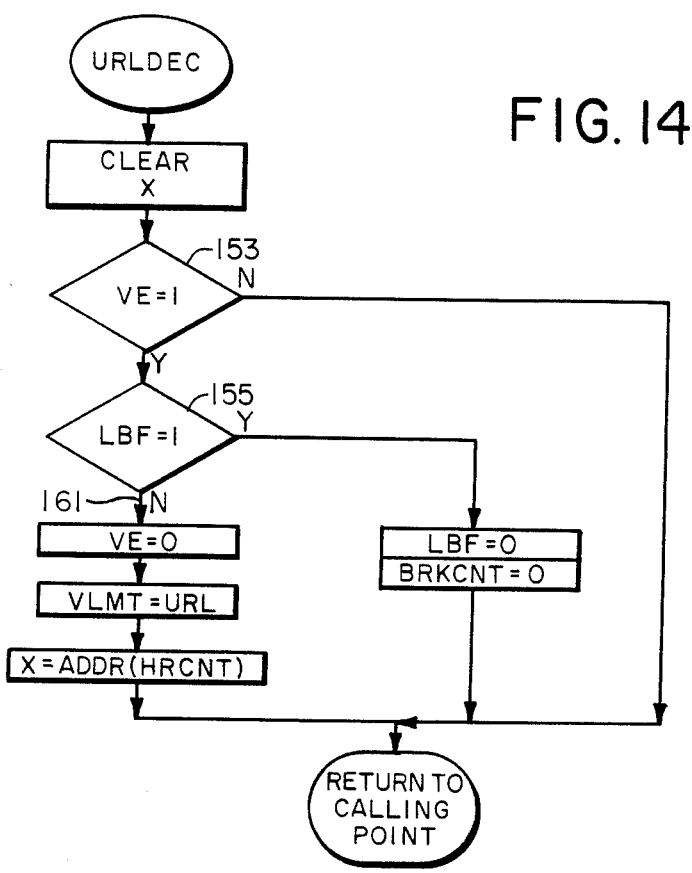

If T2 has timed out, program control is transferred to the URLDEC subroutine of FIG. 14 wherein a flag VE is tested at 153 to determine if the presently defined ventricular rate limit interval VLMT is greater than the predefined upper rate limit value URL. If VE is one, VLMT is greater than URL and program control is therefore transferred to a test at 155, wherein it is determined if the ventricle was paced on the last cycle at the defined ventricular rate limit interval VLMT. This test is performed by interrogating the state of a last beat fast bit (LBF). If LBF is equal to zero, the previous ventricular pace interval was greater than the defined ventricular rate limit interval VLMT and the previous pace was therefore a slow one. However, if LBF is equal to 1, the previous ventricular pace was provided at the defined ventricular rate limit interval VLMT and the previous ventricular pace was therefore a "fast" one.

Figure 15:
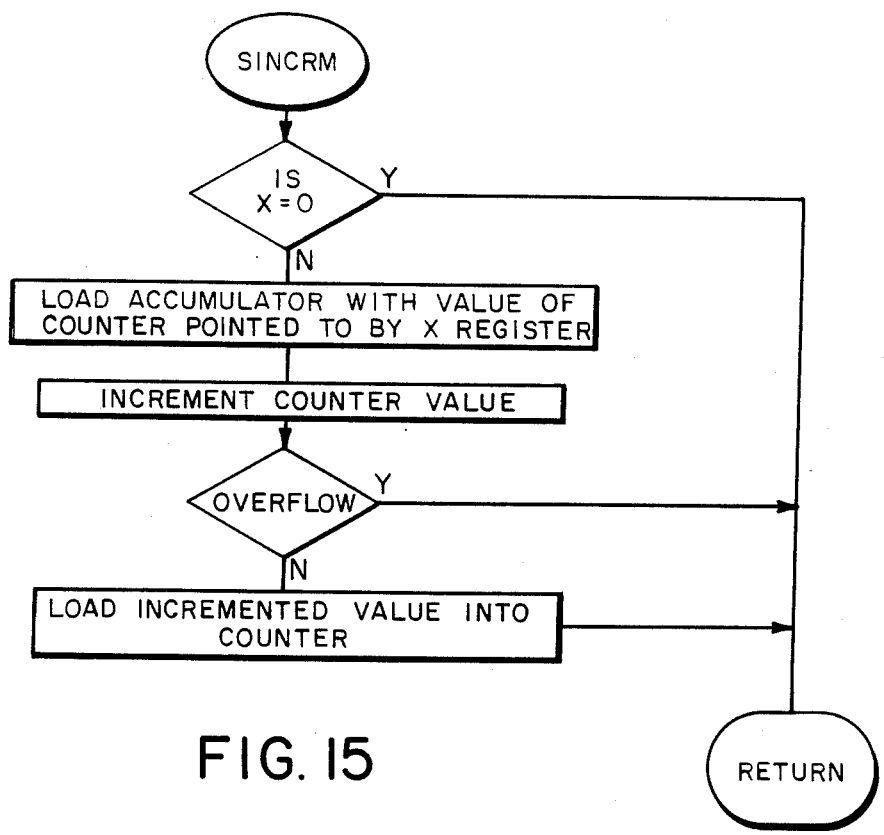

If LBF equals one, the previous ventricular pace was at the defined ventricular rate limit and there is therefore no preceding slow pace or sense, as illustrated by the ventricular pace 73 of FIG. 8. In this instance LBF is set equal to zero to indicate that the present ventricular pace is a slow one and that the previous ventricular pace was a fast one. Thereafter, the counter BRKCNT for ventricular paces at the ventricular rate limit is set to zero, because now a relatively slow ventricular beat has occurred. Thereafter program control is transferred to the point 159 of FIG. 10 at which point the SINCRM subroutine of FIG. 15 is called.

The SINCRM subroutine applies the address stored in X to access and increment an appropriate diagnostic counter. Since X is zero at this point, control is transferred to the FLAG test 233 of FIG. 10 with no action having been taken.

If the previous ventricular event had occurred at a rate slower than the defined ventricular rate limit, LBF would have been equal to zero when the URLDEC subroutine was called. In this event the test at 155 of FIG. 14 passes program control to a point 161 to indicate that the present ventricular event and the preceding ventricular event occurred at a rate less than the ventricular rate limit. Thus, for example, program control is transferred to the point 161 when the ventricular pace 76 of FIG. 8 is generated. As explained with respect to FIG. 8, two successive ventricular events occurring at intervals greater than the defined ventricular rate limit interval VLMT will cause the ventricular rate limit interval to be reset to the predefined upper rate limit value URL. Thus, as shown in FIG. 14, program control moves from the point 161 to clear the VE flag and set the ventricular rate limit interval VLMT to the upper rate limit value URL. The flag VE was set to zero to indicate that the ventricular rate limit interval VLMT is now not lengthened over the upper rate limit URL. Finally, X is loaded with the address of a high rate diagnostic counter.

The loading of X with the address of the high rate diagnostic counter (HRCNT) sets up a condition whereby the counter can be incremented to show that the pacer has recorded an incidence of ventricular pacing at the ventricular rate limit. Program control is then returned to point 159 of of FIG. 10 and the subroutine SINCRM is called to increment the diagnostic register which is addressed by X.

It should be understood that, if the code of FIG. 14 is entered as a result of slow ventricular beats occurring after VLMT has been reset to URL, the test at 153 will determine that VLMT is not greater than URL and program control will therefore be transferred out of the subroutine. This logic branch is necessary in order to ensure that the high rate diagnostic count register HRCNT is incremented only when the pacer has detected atrial events occurring at a rate greater than the ventricular rate limit and then has detected a slowing of the atrial rate to the extent that two successive ventricular paces are provided at a rate less than the ventricular rate limit.

As explained above, when program control is transferred to the point 159 of FIG. 10, the subroutine SINCRM of FIG. 15 is called to increment the diagnostic counter which is defined by the address in X. As shown in FIG. 15, if X is nonzero, an accumulator of the pacer is loaded with the count state of the counter defined by the address in the X register. The counter is then incremented and, if there is no overflow, the incremented value is loaded into the counter and control is then returned to the FLAG test 233 of the flowchart of FIG. 10. If there is an overflow, the previous value of the diagnostic register is retained.

Thus, if, for example, the subroutine of FIG. 14 is operated to load the address of the high rate diagnostic count into X, the subroutine of FIG. 15 is called to increment the counter and thereby indicate the incidence of high rate atrial events. The counter will be incremented for each incidence of such high rate events and may be accessed to determine the history of such events for a particular patient.

After the subroutine of FIG. 15 has completed its incrementation of a diagnostic counter or has determined that there is a counter overflow, FLAG is tested at 233 of FIG. 10 to determine if the pacer is operating in state 4. State 4 is utilized to time the nonphysiological delay of the pacer. As indicated above, the pacer is presently operating in state 3 and therefore, program control is transferred to make the atrial input refractory and to check a temporary marker bit at 169 to determine if the pacer has been requested to generate a 25 microsecond pulse to indicate that a ventricular event has been sensed. If the marker bit is equal to 1, the pulse will be generated to indicate the detection of a ventricular event and, if the marker bit is not equal to 1, a marker pulse will not be generated.

Thereafter, the timer T3 is set to the noise sense time NSTM of, for example, 136 milliseconds. Also, the timer T2 is set to begin timing the presently defined ventricular rate limit interval VLMT. Program control will then be returned to START 101 of FIG. 10. FLAG, NCNT, NP, T3W and T2W will be set as indicated above and the microprocessor will be returned to the sleep state at 100 to await the time out of the noise sense time or the detection of ventricular events. It should be understood that the transfer of control under the above conditions indicates that a proper ventricular event has been sensed outside of the nonphysiological interval of the pacer.

If a ventricular event is sensed when FLAG is equal to 3 and T2 has not timed out, it is known that a "fast" ventricular event has occurred at an interval that is less than the defined ventricular rate limit interval VLMT. In this event, program control is transferred to the FLAG test at 233 and, because FLAG is 3, through the marker bit code, through START 101 of FIG. 10, and to the sleep state at 100. FLAG, NCNT, NP, T3W and T2W are set as indicated above.

It will be recalled that, if the timer T3 times out during the quiet time of state 1, the microprocessor leaves its sleep state and transfers to the point 113 of FIG. 13A, at which the timer T3 is tested. If T3 has timed out, as explained above, control is transferred to the test 139 for FLAG equal to 1. Since FLAG is equal to 1, program control is transferred to 141-146 of FIG. 13B to determine if the pacer is sensing in the ventricle and the atrium and to continue the quiet time if in either case the sensing lead has a high voltage level. Thereafter the contents of AR is tested. If AR is not equal to zero, FLAG is set to 2, the timer T3 is set to AR and the atrial wake up bit AW is disabled. If the contents of AR is equal to zero, then the atrial refractory period ends at the same time as the ventricular refractory period and therefore FLAG is set to 3 and the AR interval of the next timing cycle is set to its programmed value of PROGAR. T3W is then disabled so that T3 will not wake up the microprocessor. This is done because T3 is not timing anything of relevance. After the test of AR and associated program steps, the microprocessor is put in the sleep state.

If AR was not equal to zero and thereafter the timer T3 times out, the processor wakes up and transfers program control to the T3 time out test at 113 of FIG. 13A. Since T3 has timed out, program control is transferred to a FLAG test at 191. Since FLAG equals 2, the program next determines at 162 of FIG. 13B if the pacer is operating in a mode which senses atrial events. If, for example, the pacer is operating in the VDD or DDD mode, it is sensing atrial events and the program therefore transfers control to a point 193 at which the voltage level on the atrial input sense lead is checked. If a high voltage is detected, an atrial event is still being sensed on the lead. Therefore, the AR time is prolonged by transferring the STQT of FIG. 10, loading the interval QT (64 milliseconds) into the timer T3 and then putting the microprocessor to sleep. Thereafter, when T3 times out and the microprocessor wakes up program control is transferred in the above-indicated fashion to the program point 193 of FIG. 13B. At this time there is no high signal at the atrial input lead and therefore the AW bit is enabled so that the processor will wake up if atrial events are detected. Of course, the AW bit is enabled here because the processor is operating outside the atrial refractory interval (i.e. the timer T3 has timed out the atrial refractory interval) and atrial events should therefore be sensed. The pacer checks the LBF bit to determine whether or not the last ventricular event was a pace at the ventricular rate limit and, if it was (i.e., LBF=1), the VA interval is increased by 300 milliseconds. The increased value of VA is then loaded into the timer T1 so that the timer can begin timing the extended VA interval. This increase of the VA interval was previously discussed with respect to the timing diagram of FIG. 7. It will be recalled that in that case the VA interval was increased by 300 milliseconds when a ventricular pace was provided at the ventricular rate limit.

After T1 is set to its increased VA interval, the program sets the atrial refractory interval AR equal to its programmed value and, because the atrial refractory period is over, FLAG is set equal to 3 and the T3W bit is disabled so that the microprocessor will not wake up if T3 times out. T3W is disabled because at this point T3 is not timing anything of relevance. The microprocessor is thereafter placed in the sleep state to allow T1 to time out the VA delay. It should now be understood that if an atrial event is detected during the timing out of the VA interval, the pacer will not pace the atrium. However, if an atrial event is not detected within the VA interval, the pacer will pace the atrium at the end of the VA interval, assuming that the pacer is operating in the DDD mode and no PVC is detected.

Figure 13B:
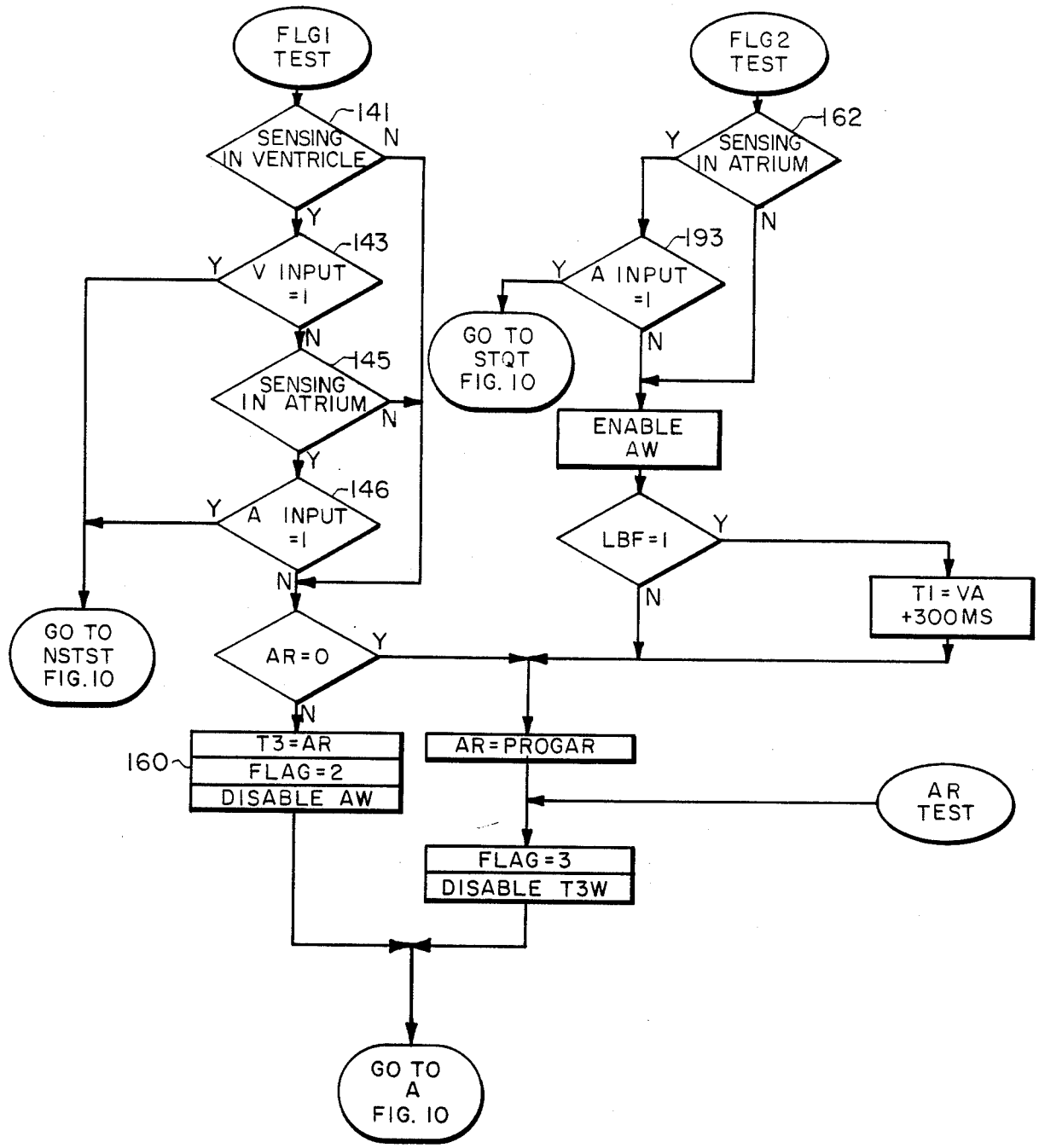

It should be understood that, if the pacer is operating in state 2 and it is also operating in a mode which does not sense the atrium, the test at 162 of FIG. 13B will transfer control around the voltage test of 193 to the point at which the AW bit is enabled. This transfer avoids a test of the voltage on the atrial input, because the test would be meaningless when the pacer is not monitoring the atrium.

When the microprocessor is in its sleep state and the VA delay of T1 is timing out, an atrial event can be sensed. If an atrial event is sensed, the processor will wake up and will transfer to a point 200 of FIG. 13A at which the condition of A LATCH is tested. The A LATCH will have been activated as a result of the sensed atrial event and the program will therefore clear the latch at 201 and check the status of FLAG. If FLAG equals 1, the atrial event has been sensed in the quiet time of the pacer and the sensed event is therefore recognized as possible noise. Accordingly, the program will transfer to the noise sense code 107 of FIG. 10 to restart the quiet time in the presence of noise.

If FLAG is not equal to 1, the sensed atrial event is then assumed to be a proper atrial event and the timer T3 is therefore loaded at 203 to begin timing an AV delay after the sensed atrial event. Thereafter a TEMP BIT3 is checked to determine if a marking pulse should be generated to indicate that an atrial event has been sensed. If the bit is equal to 1, a 25 microsecond pulse is generated by a MARKPACE subroutine and thereafter the bit T3W is enabled so that the processor will wake up when the AV delay has timed out. If the bit is not equal to 1, the MARKPACE subroutine will not be called and the T3W bit will be enabled immediately after T3 begins timing the AV delay. FLAG is set equal to 6 to indicate that the pacer is operating in state 6 to time an AV delay after a sensed atrial event.

The status register STATUS is thereafter set equal to 101 to indicate that the processor has just sensed an atrial event. The atrial amplifier is then disabled because, during the timing of the AV delay, the pacer is in an atrial refractory condition. The processor is returned to its sleep state to await the timing out of the AV interval by T3.

When T3 times out, the microprocessor wakes up and recognizes at the program point 113 of FIG. 13A that T3 has timed out. The timed out condition of T3 causes the program to check the condition of FLAG and, because FLAG is equal to 6, the program branches to a point 205 to set up a pace condition for the ventricle. The T2W bit is therefore enabled so that the processor may test the timer T2 to determine whether the ventricular rate limit interval has timed out.

T2 is then checked at 108 to determine if it has timed out. If T2 has timed out, the AV delay has therefore timed out at a time after the presently defined ventricular rate limit interval. Accordingly, the ventricular pace which is to be generated will occur at a rate that is less than the ventricular rate limit and therefore this ventricular pace is at a relatively "slow" rate. It is therefore known that the pacer is tracking atrial events of the heart and is pacing the ventricle of the heart at a rate that is less than the ventricular rate limit. Accordingly, the previously described URLDEC subroutine of FIG. 14 is called to determine if the present slow ventricular pace is the first or second slow ventricular pace occurring after preceding ventricular paces at the ventricular rate limit. The subroutine of FIG. 15 is then called to increment the high count diagnostic register if a second slow ventricular interval has occurred after previous ventricular paces at the ventricular rate limit. Program control is then transferred to a point 209 of FIG. 11 after which T3 is set to begin timing the noise sense time, T1 is set to time a nonfunctional delay interval, the BRKCNT variable is checked in a previously described manner, and the ventricle is paced if BRKCNT is not equal to 15.

It should be understood that under the presently described circumstances wherein a slow ventricular pace is to be generated, the variable BRKCNT will equal 0. Accordingly, the ventricle will be paced and the status register STATUS will be "ORed" with the bit pattern 010. which sets the middle bit of STATUS to a 1. The pacer will then be returned to START 101 of FIG. 10 and will thereafter set variables and return to the sleep state, as previously described.

It should be understood that if the variable BRKCNT had been equal to 15, the variable would have been set equal to zero and FLAG would have been set to 8 to indicate that the processor was about to skip a ventricular pace and was therefore waiting to sense something in either the atrium or the ventricle. Thereafter the AW bit is enabled so that the processor will wake up in the event that a natural atrial event is detected. Program control is then returned to a SKPPAC point 211 of FIG. 10, the nonphysiological flag is thereafter set to zero, the bit T3W is enabled, the bit T2W is disabled and the processor is placed in the sleep state.

It should be recalled that the immediately preceding program sequence was initiated by the detection of an atrial event, the subsequent initiation of a program state 6 and the timing out of an AV delay in T3 and the ventricular rate limit interval in T2. If, however, T3 times out in state 6 and the T2 test at 108 of FIG. 13A shows that T2 has not timed out, then it is known that the AV delay has timed out within the presently defined ventricular rate limit interval, as illustrated in the timing diagram of FIG. 7. Therefore, program control is transferred to a point 213 at which FLAG is set equal to 7 to indicate that the processor is operating in a state wherein the AV delay must be prolonged in order to wait for the ventricular rate limit interval to time out. After FLAG is set equal to 7, the processor is returned to the sleep state to await the timing out of T2 or a sensed ventricular event.

Figure 16:
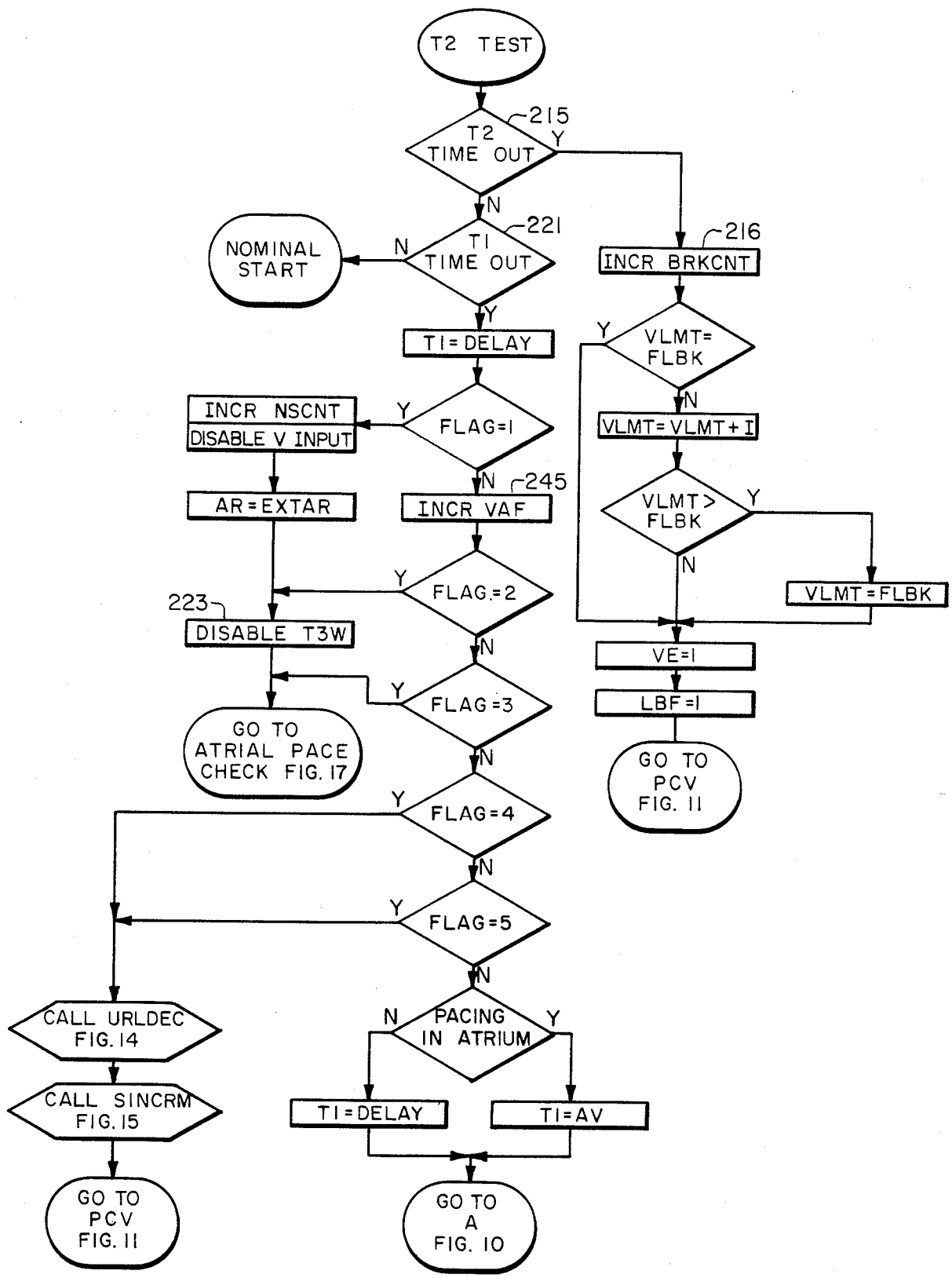

When T2 times out, the processor wakes up and, as shown in FIGS. 10, 13A and 16, successively tests the V LATCH, A LATCH, timer T3 and finally the timer T2 at 215 of FIG. 16. Since the timer T2 has timed out and the T2W bit has been set, the processor increments BRKCNT at 216 to indicate that a ventricular pace is about to be generated at the currently defined ventricular rate limit. The program next determines if the ventricular rate limit interval VLMT is presently equal to the fallback rate limit value FLBK. If the ventricular rate limit interval VLMT is not equal to the fallback rate limit value, the program increments the ventricular rate limit by an amount I, as explained previously with respect to the timing diagram of FIG. 7. Thereafter, the program checks to see if the added incremental amount has made the ventricular rate limit interval VLMT greater than the programmed fallback value FLBK. If it is greater, the ventricular rate limit VLMT is set equal to the fallback rate limit value and, if it is not greater, the incremented value of VLMT is retained.

Thereafter the flag bit VE is set equal to 1 to indicate that the ventricular rate limit has been extended with respect to the URL value. It will be recalled that the VE bit was checked in the subroutine of FIG. 14 to determine if the ventricular rate limit interval VLMT was greater than the programmed upper rate limit interval URL. Of course, if VE equals one it is known that VLMT has been incremented to an amount greater than the upper rate limit value URL. After VE is set, the last beat fast bit LBF is set equal to 1 to indicate that the present ventricular pace is being made at the ventricular rate limit and is therefore not a slow pace. It will be recalled that the LBF bit was checked in the subroutine of FIG. 14 to determine whether or not two slow ventricular paced or sensed events follow ventricular paces at the ventricular rate limit.

After the LBF bit is set, program control is returned to the PCV point 209 of FIG. 11 in order to pace the ventricle. As previously explained, code is executed to set T3 to time a noise sense interval and T1 is set to time a delay interval. The variable BRKCNT is checked to determine if 15 ventricular paces at the ventricular rate limit have been generated. If so, as explained previously with respect to FIG. 9, a ventricular pace is skipped.

It should be understood that if the program determines that T2 has timed out at the T2 test point 215 of FIG. 16, and the ventricular rate limit interval VLMT is equal to the fallback rate limit value FLBK, VLMT will not be further incremented and program control will therefore be branched around the abovedescribed VLMT incrementing code and will then set the VE and LBF bits and pace the ventricle in the abovedescribed manner.

If FLAG is set equal to 8 as shown in FIG. 11 as a result of a BRKCNT of 15, program control will be transferred to SKPPAC of FIG. 10 and the pacer will skip a ventricular pace and will be placed in the sleep state. T3 will thereafter time out a noise sense interval of, for example, 136 milliseconds. When T3 times out, the processor will wake up and the T3 test 113 of FIG. 13A will check the status of FLAG. If it is found at 194 that FLAG is not 8, the value of FLAG is unrecognizable and the program is therefore branched to a nominal start to restart its operation. If FLAG is 8, the timer T1 will be set to begin timing a VA delay approximately 136 milliseconds after the point at which a ventricular pace was inhibited (see point 85 of FIG. 9 and defined VA interval). Thereafter FLAG will be set equal to 3 at FIG. 13B, the T3W bit will be disabled so that the processor will not wake up on a time out of T3 and the processor will then be placed in the sleep state.

The time T1 is employed, as explained above, to time out the VA delay which follows a sensed or paced ventricular event. If T1 times out while the microprocessor is in its sleep state, the processor will wake up and will check the status of the V LATCH, A LATCH, and timers T3, T2 and T1. When T1 is checked, as shown at 221 of FIG. 16, it is determined that it has timed out and therefore T1 is set to time a delay interval and the status of FLAG is checked. If FLAG equals 1, the VA delay has timed out while the pacer is in the quiet time and it is therefore known that noise has occurred. A diagnostic counter NSCNT is incremented to show that a noise interruption has occurred and the ventricular amplifier is disabled because noise is present. Thereafter the atrial refractory interval AR is extended to EXTAR, because the pacer is operating in a noise reversion mode and, when it eventually leaves the noise reversion mode, a pacer sustained tachycardia condition must be avoided in the case where the pacer is operating in either the VDD or DDD mode. Since T1 has timed out in a noise reversion situation, the pacer is committed to asynchronously pace the ventricle.

The T3W bit is disabled at 223 of FIG. 16 to ensure that the processor will not wake up on the timing out of the quiet time of T3. Thus, by disabling T3W, the pacer ignores either any quiet time that remains or the timing of the atrial refractory period. The timer T1 is then set at 231 of FIG. 17 to begin timing the AV delay and the mode of the pacer is checked at 241 to determine if the pacer is operating to pace the atrium.

If the pacer is operating to pace the atrium, circuitry of the pacer is configured to start a ventricular blanking interval and the timer T3 is loaded to begin timing a nonphysiological delay. Thereafter the atrium is paced at 250, the status register STATUS is set to 001 in order to indicate that the atrium has been paced and a timer T4 is loaded to begin timing a first blanking interval for ventricular events. The processor is thereafter put to sleep until the timer T4 times out the end of the first blanking period and thereafter the timer T4 is set to begin timing a second blanking interval and FLAG is set equal to 4 to indicate that the pacer is operating in a state wherein the nonphysiological delay is being timed. The atrial amplifier is thereafter disabled and the microprocessor is maintained in its sleep state until the end of the second blanking interval. Thereafter the T3W bit is enabled so that, when the pacer is put to sleep, it will wake up when T3 has completed its timing of the nonphysiological AV delay. The processor is then put to sleep.

When the timer T3 times out the nonphysiological AV delay, the T3 test at 113 of FIG. 13A transfers program control to a point 225 at which it is determined that FLAG is equal to 4. At this point it is known that T3 has timed out the nonphysiological AV delay, but it is not known if signals were detected during the delay. A nonphysiological flag NP FLAG is therefore checked to determine if signals were detected during the nonphysiological delay. If NP FLAG equals 1, signals were detected during the nonphysiological delay and therefore, the ventricle must be paced at a time defined by a nonphysiological ventricular pace interval (NPVI) which independently defines a ventricular pace time when a ventricular event is detected during the nonphysiological delay. Thus, FLAG is set equal to 9, T3 is set to time out NPVI, T3W is enabled and the processor is put to sleep.

When T3 times out, program control is transferred to the FLAG test 196 of FIG. 13A and, since FLAG is equal to 9, the T2W bit is enabled to allow a test of the timer T2. The timer T2 is checked at 108 to determine if the ventricular rate limit interval has timed out. If it has not, FLAG is set to 7 at 213 in order to prolong the AV delay and therefore wait until the timer T2 times out the ventricular rate limit interval. Alternatively, if T2 has timed out, the subroutines of FIGS. 14 and 15 are called in the manner described above and the ventricle is paced, as shown at FIG. 11.

If, after the flag check at 225 of FIG. 13A it is determined that NP FLAG is not equal to 1, then no signal was detected during the nonphysiological AV interval. Therefore, FLAG is set equal to 5 at 229 to indicate that the microprocessor is operating in a state required to time an AV delay after a paced atrial event. Thereafter program control is returned to the point 102 of FIG. 10 and the processor is put to sleep. The processor will be awakened when the timer T1 times out the rest of the AV delay, which was initiated at a point 231 of FIG. 17.

It should now be understood that, when the nonphysiological AV delay is timing out and a ventricular signal is sensed, the microprocessor will wake up and will check V LATCH 103 of FIG. 10. Thereafter the processor will clear V LATCH at 105 and will check FLAG. It will be determined at the point 233 of FIG. 10 that FLAG is equal to 4 and, therefore, the NP FLAG bit will be set. This bit is set because a ventricular signal has been detected within the nonphysiological AV interval. Thereafter the ventricular sense amplifier will be disabled to make the ventricular sensing circuitry refractory and not to allow a wake up on a ventricular event. It should be appreciated at this point that the ventricular refractory condition is initiated so that a natural ventricular event will not be detected. This is done because, when an event is detected during a nonphysiological AV delay, the pacer is committed to pacing the ventricle either at the end of the nonphysiological delay or at some predefined time following the delay, as explained above.

After the ventricular circuitry is made refractory, the bit T2W is disabled so that the microprocessor will not wake up when the ventricular rate limit timer T2 times out. Thereafter the processor is put in the sleep state to await the timing out of the nonphysiological AV delay by T3.

It will be recalled from the above discussion that at the point 221 of FIG. 16 it was determined that the timer T1 timed out a VA or an AV delay. It was thereafter determined that FLAG was equal to 1 and later it was determined at 241 of FIG. 17 that the pacer was operating in a mode in which the atrium would be paced. If at the point 241 it is determined that the pacer is operating in a mode wherein the atrium is not paced, program control is passed to a point 243 at which FLAG is set to 5. Thereafter the status register STATUS is set equal to 001 to indicate the appropriate status condition at this point and the atrial sense amplifier is disabled, because the program has defined an atrial refractory interval at this point. The microprocessor is then put in the sleep state to wait for T1 to time out the AV delay.

If T1 times out a VA or AV delay, the microprocessor wakes up and transfers to the point 221 of FIG. 16 at which it is determined that T1 has timed out. Thereafter T1 is set to time a delay interval and, if FLAG is not equal to 1, the variable VAF is incremented at 245. It should be understood that if VAF is equal to 2, the timer T1 has timed out an AV delay. When VAF is equal to zero, the timer T1 has timed a VA delay. When VAF is incremented to 1, T1 will be set to time the AV delay. Therefore, for as long as VAF equals 1, the timer T1 is timing the AV delay.

After VAF is incremented, FLAG is checked to determine if it is equal to 2. If FLAG is equal to 2, the VA delay has timed out and nothing has been sensed in the atrium. In this event it is known that noise of some kind has occurred. Accordingly, the program transfers to the point 223 to disable the bit T3W and to thereby ignore any time left in T3 for the atrial refractory period. Thereafter T1 is set to time the AV delay and at 241 of FIG. 17 the program determines whether or not to pace the atrium. The results of this decision have been previously discussed in detail and therefore should be fully understood at this time.

If, after incrementing VAF, FLAG is not equal to 2, FLAG is tested to determine if it is equal to 3. If FLAG equals 3, T1 has timed out the VA delay and nothing has been sensed in the atrium during the VA delay. Accordingly, it is necessary at this point to pace the atrium. Therefore, program control is transferred to the point 231 to start the timer T1 to time the AV delay and the program then moves to the point 241 to decide whether or not the pacer is operating in a mode which allows pacing of the atrium. The subsequent steps have been previously discussed in detail.

If, as shown in FIG. 16, the timer T1 has timed out its interval and FLAG is not equal to 3, the program then checks to see if FLAG is equal to 4. If FLAG equals 4, the nonphysiological interval is greater than the AV delay and the pacer is therefore operating in the committed mode (i.e., the pacer is operating so that an atrial event is always followed by a pace in the ventricle). The program then calls the subroutines of FIGS. 14 and 15 in order to determine if two immediately preceding ventricular pace or sense events have occurred at intervals longer than the ventricular rate limit interval. Thereafter the ventricle is paced in the manner shown in FIG. 11.

If, as shown in FIG. 16, T1 times out and FLAG does not equal 4, the program checks to determine if FLAG equals 5. If FLAG is equal to 5, it is known that T1 has timed out the AV interval and that the pacer has paced in the atrium and has not sensed in the ventricle. Accordingly, program control is transferred to call the subroutines of FIGS. 14 and 15 and to pace the ventricle, as shown in FIG. 11. If FLAG is not equal to 5, the pacer then checks to determine if VAF is equal to 1. If VAF equals 1, the VA interval has just ended and the timer T1 is set to begin timing the AV delay. However, if VAF is not equal to 1, the timer T1 is set to begin timing a nonfunctional delay. In either case the processor is returned to the sleep state to await a sensed awaking event or a time out condition.

The microprocessor program of the system of FIG. 1 has been described in detail to illustrate a means whereby the advantageous pacing functions of the invention may be achieved. However, it should be understood that the program steps and interval values are provided for illustrative purposes only and are not intended to limit the scope of the invention. Accordingly, the invention may be embodied in other specific forms without departing from its spirit or essential characteristics. The present embodiment is, therefore, to be considered in all respects as illustrative and not restrictive, the scope of the invention being indicated by the claims rather than by the foregoing description. Accordingly, all changes which come within the meaning and range of the equivalents of the claims are intended to be embraced therein.

We claim:

1. A pacemaker for monitoring cardiac activity of a heart and for pacing the heart, comprising:
   means for sensing electrical signals in the ventricle of a heart;
   means for sensing electrical signals in the atrium of the heart;
   timing means for timing an atrial refractory period having a first preselected duration when an electrical signal occurs in the ventricle while connective tissue between the atrium and ventricle is refractory and a second greater duration when an electrical signal occurs in the ventricle while said connective tissue is operative to allow retrograde conduction of the signal from the ventricle to the atrium, said second greater duration ensuring that a signal transmitted from the ventricle to the atrium by retrograde conduction will fall within the atrial refractory period when it reaches the atrium; and means for pacing the ventricle at a predetermined time period after an electrical signal is sensed in the atrium outside said atrial refractory period.

2. The pacemaker of claim 1 wherein said timing means includes means for timing an atrial refractory period of said second duration for one cycle upon detecting a premature ventricular contraction following a ventricular event.

3. The pacemaker of claim 1, wherein said timing means includes means for timing an atrial refractory period of said second duration after sensing a premature ventricular contraction following a pace of the ventricle.

4. The pacemaker of claim 1, wherein said timing means includes:

means for selecting a nominal ventricular pacing rate at which to pace the ventricle in the absence of sensed atrial events; and means for timing an atrial refractory period of said second duration after pacing the ventricle in the VDD pacing mode and sensing an atrial rate less than a rate defined by the sum of the period of said nominal ventricular pacing rate and a time required for retrograde conduction of electrical signals from the ventricle to the atrium.

5. The pacemaker of claim 1, wherein said timing means includes means for timing an atrial refractory period of said second duration for one cycle after pacing the ventricle and sensing an atrial bradycardia in a VDD pacing mode.

6. The pacemaker of claim 1, wherein said timing means includes means for timing an atrial refractory period of said second duration when a ventricular pace in the VDD mode is not initiated by a preceding sensed electrical signal in the atrium.

7. The pacemaker of claim 1, including means for selectively operating in either fixed rate pacing modes or in at least one other mode wherein atrial signals are sensed to pace the ventricle, and wherein said timing means includes means for timing an atrial refractory period of said second duration when a signal occurs in the ventricle following a change from a fixed rate pacing mode to said at least one other mode.

8. The pacemaker of claim 1, including means for operating in a noise reversion mode to asynchronously pace the ventricle in response to sensed noise and for operating in at least one other mode wherein atrial signals are sensed to pace the ventricle, and wherein said timing means includes means for timing an atrial refractory period of said second duration when a signal occurs in the ventricle following a change from said noise reversion mode to said at least one other mode.

9. The pacemaker of claim 1, including means for operating in a telemetry mode to transmit telemetry signals and asynchronously pace the ventricle and for operating in at least one other mode wherein atrial signals are sensed to pace the ventricle, said timing means including means for timing an atrial refractory period of said second duration when a signal occurs in the ventricle following a change from said telemetry mode to said at least one other mode.

10. The pacemaker of claim 1, wherein said timing means includes means for defining said second greater duration as a time period that is greater than the time required for an electrical signal to be conducted to the atrium by retrograde conduction from the ventricle.

11. The pacemaker of claim 1, including means for selectively operating in either the VDD or DDD modes or in at least one mode where signals are not sensed in the atrium, and wherein said timing means includes means for timing an atrial refractory period of said second duration for one cycle when a signal occurs in the ventricle following a change from said at least one mode to said VDD or DDD mode.

12. The pacemaker of claim 1, including means for selectively operating in a first mode wherein the atrium is paced but not sensed or in either the VDD or DDD modes, said timing means including means for timing an atrial refractory period of said second duration for one cycle when a signal occurs in the ventricle following a change from said first mode to either said VDD or DDD modes.

13. The pacemaker of claim 1, including means for selectively operating in fixed rate pacing modes and modes wherein atrial signals are sensed to pace the ventricle, said timing means including means for timing an atrial refractory period of said second duration for one cycle when a signal occurs in the ventricle following a change from a fixed rate mode to any other mode.

14. A pacemaker for monitoring cardiac activity and pacing the heart, comprising:

means for sensing electrical events in the atrium of the heart;

means for sensing electrical events in the ventricle of the heart;

means for timing out an atrial refractory period having a first preselected duration in response to the sensing of an electrical event in the ventricle or to the pacing of the ventricle in the absence of a retrograde conduction condition between the atrium and ventricle;

means for timing out an atrial refractory period having a second preselected duration in response to the sensing of a retrograde conduction condition between the ventricle and atrium and the sensing of an electrical event in the ventricle or the pacing of the ventricle, said second duration defined so that a retrograde conducted atrial signal will fall within the atrial refractory period; and means for pacing the ventricle at a predefined AV time period after the sensing of an atrial event outside said atrial refractory period.

15. A method of operating a pacemaker to avoid pacemaker sustained tachycardia, comprising the steps of:

detecting electrical signals which occur in the atrium and ventricle of a heart;

selecting first and second durations for an atrial refractory interval, said second duration greater than said first duration;

timing out an atrial refractory interval of the first duration when an electrical signal occurs in the ventricle in the absence of a retrograde conduction condition between the atrium and ventricle;

pacing the ventricle after a predefined time period following the detection of a signal in the atrium, unless the signal in the atrium occurs while the atrial refractory interval is timing out;

sensing at least one heart condition that may allow retrograde conduction of electrical signals from the ventricle to the atrium; and timing out an atrial refractory interval of the second duration for one cycle when an electrical signal occurs in the ventricle and said at least one heart condition is sensed, so that the signal transmitted to the atrium by retrograde conduction falls within the atrial refractory interval and therefore does not initiate a pace of the ventricle.

16. The method of claim 15, wherein the step of sensing at least one heart condition includes sensing a premature ventricular contraction.

17. The method of claim 15, wherein the step of sensing at least one heart condition includes sensing a premature ventricular contraction following a pace of the ventricle.

18. The method of claim 15, wherein the step of sensing at least one heart condition includes sensing a change from a fixed rate mode of operation of the pacemaker to a VDD or DDD mode of operation of the pacemaker.

19. The method of claim 15, wherein the step of sensing at least one heart condition includes sensing a ventricular pace in the VDD mode whichis not initiated by a preceding sensed atrial signal.

20. The method of claim 15, wherein the step of sensing at least one heart condition includes sensing an atrial bradycardia in the VDD pacing mode.

21. The method of claim 15, wherein said step of sensing at least one heart condition includes detecting a change from a noise reversion mode of the pacemaker to a mode wherein atrial signals are sensed to pace the ventricle.

22. The method of claim 15, wherein said step of sensing at least one heart condition includes detecting a change from a telemetry transmission mode of the pacemaker to a mode wherein atrial signals are sensed to pace the ventricle.

23. The method of claim 15, wherein said step of sensing at least one heart condition includes detecting a change from an asynchronous ventricular pacing mode of the pacemaker to a mode wherein atrial signals are sensed to pace the ventricle.

24. A pacemaker for sensing electrical events in the atrium and ventricle of a heart and pacing the heart in a manner which avoids pacemaker sustained tachycardia, comprising:
means for selecting a value for a ventricular rate limit which defines the maximum rate at which the ventricle can be paced;
means for sensing electrical events in the ventricle;
means for sensing an electrical event in the atrium and pacing the ventricle if no ventricular event is sensed within a predefined AV delay following the sensing of the event in the atrium, the ventricle being paced at the end of the AV delay if the pace would not exceed the ventricular rate limit and being otherwise paced at the ventricular rate limit;
means for counting successive paces of the ventricle at the ventricular rate limit;
means for inhibiting a pace of the ventricle when the number of successive ventricular paces at the ventricular rate limit is equal to a predetermined value;
means for selecting a value of an atrial refractory interval and for timing the interval from a sensed or paced ventricular event;
means for preventing a ventricular pace in response to electrical events occurring in the atrium during the atrial refractory interval;
means for detecting at least one condition which could cause a spurious atrial event to appear in the atrium as a result of retrograde conduction of an electrical signal from the ventricle to the atrium; and
means for extending the atrial refractory interval a predetermined amount in response to the detection of said at least one condition, so that said spurious atrial event will not initiate a pace of the ventricle.

25. A pacemaker for sensing electrical events in the atrium and ventricle of a heart and for pacing the heart, comprising:
means for selecting a value of a ventricular rate limit which defines the maximum rate at which the ventricle can be paced;
means for sensing electrical events in the ventricle;
means for sensing an electrical event in the atrium and pacing the ventricle if no ventricular event is sensed with a predefined AV delay following the sensing of the event in the atrium, the ventricle being paced at the end of the AV delay if the pace would not exceed the ventricular rate limit and being otherwise paced at the ventricular rate limit;
means for selecting an upper rate limit value and a fallback rate limit value for the ventricular rate limit, the pacing rate defined by the fallback value being equal to or less than the pacing rate defined by the upper rate limit value;
means for setting the ventricular rate limit equal to the upper rate limit value and for reducing the ventricular rate limit thus defined to the fallback rate limit value in predefined decremental steps, the ventricular rate limit being decremented for each ventricular pace occurring at the then defined ventricular rate limit;
means for selecting a value of an atrial refractory interval and for timing the interval from a sensed or paced ventricular event;
means for preventing a ventricular pace in response to electrical events which occur in the atrium during the atrial refractory interval, so that a ventricular pace is periodically dropped when the ventricle is being paced at the ventricular rate limit;
means for selecting a value of an atrial refractory interval and for timing the interval from a sensed or paced ventricular event;
means for preventing a ventricular pace in response to electrical events occurring in the atrium during the atrial refractory interval;
means for detecting at least one condition which could cause a spurious atrial event to appear in the atrium as a result of retrograde conduction of an electrical signal from the ventricle to the atrium; and
means for extending the atrial refractory interval a predefined amount in response to the detection of said at least one condition, so that said spurious atrial event will not initiate a pace of the ventricle.

26. A pacemaker for sensing electrical events in the atrium and ventricle of a heart and pacing the heart in a manner which avoids pacer sustained tachycardia, comprising:
means for selecting a value for a ventricular rate limit which defines the maximum rate at which the pacemaker will pace the ventricle;
means for sensing an electrical event in the atrium and pacing the ventricle if no ventricular event is sensed within a predefined AV delay following the sensing of the event in the atrium, the ventricle being paced at the end of the AV delay if the pace would not exceed the ventricular rate limit and being otherwise paced at the ventricular rate limit;

counting means for counting successive paces of the ventricle at the ventricular rate limit and for inhibiting a pace of the ventricle when the number of successive ventricular paces at the ventricular rate limit is equal to a predefined count value;

means for defining an atrial refractory time period during which electrical events in the atrium will not cause a pace of the ventricle;

means for detecting at least one condition wherein electrical signals of the ventricle could be conducted to the atrium; and means for extending said atrial refractory period when said at least one condition is sensed, so that an electrical signal conducted from the ventricle to the atrium will fall within the extended atrial refractory period and will not cause a pace of the ventricle.

27. The pacemaker of claim 26 wherein said counting means includes means for counting to said predefined count value from a reset state and means for resetting the counting means to the reset state when a ventricular pace or sense event occurs at a rate less than the ventricular rate limit and also when the counting means counts to said predefined count value.

28. A method for operating a pacemaker to avoid pacemaker sustained tachycardia, comprising:

selecting a value for a ventricular rate limit which defines the maximum rate at which the ventricle of a heart can be paced;

sensing an electrical event in the atrium of the heart;

timing out a predefined AV delay when the atrial event is sensed;

pacing the ventricle at the end of the AV delay if the pace will not exceed the defined ventricular rate limit;

pacing the ventricle at the ventricular rate limit if a pace at the end of the AV delay would exceed the ventricular rate limit;

selecting a value for an atrial refractory interval;

timing the atrial refractory interval from a sensed or paced ventricular event;

preventing a sensed atrial event from initiating a ventricle pace when the atrial event falls within the atrial refractory interval, so that a ventricle pace is periodically dropped when the ventricle is paced at the ventricular rate limit;

monitoring pacing conditions to detect at least one condition under which retrograde conductor from the ventricle to the atrium could occur; and extending the atrial refractory interval when the at least one condition is detected, so that an atrial event occurring due to retrograde conduction will fall within the extended atrial refractory interval and will not cause a pace of the ventricle.

* * * * *